US007195890B2

(12) United States Patent
Van Eyk et al.

(10) Patent No.: US 7,195,890 B2
(45) Date of Patent: *Mar. 27, 2007

(54) METHODS AND COMPOSITIONS FOR MODULATING PROTEINS MODIFIED IN PRECONDITIONING AGAINST ISCHEMIA/HYPOXIA

(75) Inventors: Jennifer E. Van Eyk, Baltimore, MD (US); Steven T. Elliott, Cockeysville, MD (US); David Kent Arrell, Rochester, MN (US)

(73) Assignee: Queen's University at Kingston, Kingston (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/824,027

(22) Filed: Apr. 14, 2004

(65) Prior Publication Data

US 2004/0259793 A1    Dec. 23, 2004

Related U.S. Application Data

(60) Provisional application No. 60/463,139, filed on Apr. 14, 2003.

(51) Int. Cl.
*C12Q 1/26* (2006.01)
(52) U.S. Cl. ........................ 435/25; 435/7.21
(58) Field of Classification Search ............... 530/300, 530/350; 514/2, 12, 14
See application file for complete search history.

(56) References Cited

U.S. PATENT DOCUMENTS

| 4,880,783 | A | 11/1989 | Mentzer, Jr. et al. |
| 6,165,977 | A * | 12/2000 | Mochly-Rosen ............ 514/16 |
| 6,790,634 | B2 | 9/2004 | Van Eyk et al. ............ 435/21 |
| 2003/0022220 | A1* | 1/2003 | Van Eyk et al. ............ 435/6 |

FOREIGN PATENT DOCUMENTS

| CA | 2 356 499 | 2/2003 |
| WO | WO 03/004693 A2 | 1/2003 |

OTHER PUBLICATIONS

Wang, Y. et al. J. Mol. Cell. Cardiol. 33:2037-2046 (2001).*
Currie et al. Brain Research 863: 169-181 (2000) "Benign focal ischemic preconditioning induces neuronal Hsp70 and prolonged astrogliosis with expression of Hsp27".*
Kobara et al. J Mol Cell Cardiol 28: 417-428 (1996) "Effect of ischemic preconditioning on mitochondrial oxidative phosphorylation and high energy phosphates in rat hearts".*
Nakagawa et al., "ATP-dependent potassium channel mediates neuroprotection by chemical preconditioning with 3-nitropropionic acid gerbil hippocampus", Neuroscience Letters 320: 33-36 (2002).*
Tanaka et al., "Synergistic induction of HSP40 and HSC70 in the mouse hippocampal neurons after cerebral ischemia and ischemic tolerance in gerbil hippocampus", Journal of Neuroscience Research 67: 37-47 (2002).*
Ala-Rami, A., et al. "Ischaemic preconditioning and a mitochondrial KATP channel opener both produce cardioprotection accompanied by F1F0-ATPase inhibition in early ischaemia." Basic Res. Cardiol. 98: 250-258 (2003).
Bolli, R. "The late phase of preconditioning." Circ. Res. 87: 972-983 (2000).
Dana, A., et al. "Adenosine A1 receptor induced delayed preconditioning in rabbits. Induction of p38 mitogen-activated protein kinase activation and Hsp27 phosporylation via a tyrosine kinase- and protein kinase C-dependent mechanism." Circ. Res. 86: 989-997 (2000).
Hanley, P.J., et al. "Halothane, isoflurane and sevoflurane inhibit NADH: ubiquinone oxidoreductase (complex I) of cardiac mitochondria," J. Physiol. 554.3: 687-693 (2002).
Kloner, R.A., et al. "Consequences of brief ischemia: stunning, preconditioning, and their clinical implications." Circulation 104: 2981-2989 (2001).
Schafer, G., et al. "Diazoxide, an inhibitor of succinate oxidation." Biochem. Phama. 18: 2678-2681 (1969).
Schafer, G., et al. "Inhibition of mitochondrial metabolism by the diabetogenic thiadiazine diazoxide-I. Action on succinate dehydrogenase and TCA-cycle oxidations." Biochem. Phama. 20: 1271-1280 (1971).
Thornton, J., et al. "Inhibition of protein synthesis does not block myocardial protection afforded by preconditioning." Am. J. Physiol. 259: H1822-H1825 (1990).
Hanley et al., "$K_{ATP}$ channel-independent targets of diazoxide and 5-hydroxydecanoate in the heart", Journal of Physiology 2002 542.3:735-741.
Arrell et al., "Proteomic Analysis of Pharmacological Preconditioning Novel Protein Targets Converge to Mitochondrial Metabolism Pathways", Cir Res. 2006 99:706-714 with online Supplemement.
Arrell et al., "Proteomic Analysis of Pharmacologically Preconditioned Cardiomyocytes Reveals Novel Phosphorylation of Myosin Light Chain 1", Cir Res. 2001 89:480-487.
Liu et al., "Synergistic Modulation of ATP-Sensitive $K^+$ Currents by Protein Kinase C and Adenosine", Circulation Research 1996 78:443-454.
Sato et al., "Adenosine Primes the Opening of Mitochondrial ATP-Sensitive Potassium Channels: A Key Step in Ischemic Preconditioning?" Circulation 2000 102:800-805.

(Continued)

*Primary Examiner*—Robert A. Wax
*Assistant Examiner*—Anand Desai
(74) *Attorney, Agent, or Firm*—Licata & Tyrrell P.C.

(57) ABSTRACT

Proteins modified by pharmacological preconditioning are provided. Compositions, methods and events for modulating these proteins and priming cells for preconditioning and inducing preconditioning in a cell, tissue or organ as well as methods for identifying new compositions and methods for such priming and induction are also provided. In addition, methods for diagnosing and monitoring preconditioning or ischemic, hypoxic, ischemic/reperfusion and hypoxic/reperfusion conditions or the ability of a cell, tissue or organ to survive injury by measuring modulation of one or more of these preconditioning proteins are provided.

20 Claims, 12 Drawing Sheets

OTHER PUBLICATIONS

Steinberg, Robert A., "Cyclic AMP-dependent Phosphorylation of the Precursor to β Subunit of Mitochondrial $F_1$-ATPase:A Physiological Mistake?", The Journal of Cell Biology 1984 98:2174-2178.

Ylitalo et al., "Reversible ischemic inhibition of $F_1F_0$-ATPase in rat and human myocardium", Biochimica et Biophysica Acta 1504 2001 329-339.

* cited by examiner

METHODS AND COMPOSITIONS FOR MODULATING PROTEINS MODIFIED IN PRECONDITIONING AGAINST ISCHEMIA/HYPOXIA

INTRODUCTION

This patent application claims the benefit of priority from U.S. Provisional Application Ser. No. 60/463,139, filed Apr. 14, 2003, which is herein incorporated by reference in its entirety.

FIELD OF THE INVENTION

Modifications to various proteins including, but not limited to, proteins involved in the tricarboxylic acid (TCA) cycle, oxidative phosphorylation (OxPhos) pathways, calcium ($Ca^{2+}$) handling, and/or chaperoning, as well as proteins selected from aldehyde dehydrogenase, NG-dimethylarginine dimethylaminohydrolase (DDAH) and the RNA binding protein regulatory subunit DJ-1, have been identified which occur during pharmacological preconditioning, a treatment which mimics many aspects of classical ischemic preconditioning or hypoxia including protection of a cell, tissue or organ from damage resulting from prolonged periods of ischemia, hypoxia, ischemia/reperfusion, hypoxia/reperfusion or any other event or agent that causes or promotes cell death (necrosis or apoptosis) or injury. The present invention provides methods or events and compositions for modulating one or more of these preconditioning proteins as well as methods for identifying new compositions and methods or events capable of modifying one or more of these preconditioning proteins. The present invention also provides methods or events and compositions for priming a cell for preconditioning, for preconditioning a cell, tissue or organ, and/or for modulating preconditioning of a cell tissue or organ, as well as methods for identifying new compositions and methods or events for priming a cell for preconditioning, for preconditioning a cell, tissue or organ, and/or for modulating preconditioning of a cell, tissue or organ based upon the ability of the composition to modify one or more of these preconditioning proteins. In addition, the present invention provides methods for diagnosing effective preconditioning and monitoring preconditioning of a cell, tissue or organ based upon detection of one or more of these preconditioning proteins.

BACKGROUND OF THE INVENTION

Oxidative metabolism is the means by which all eukaryotic cells convert extracellular substrate (in the form of carbohydrates, lipids, and some amino acids) into adenosine 5'-triphosphate (ATP) to meet cellular energy demands. Under normal conditions, ATP production meets demand, thus pathways involved in ATP synthesis are well controlled and respond quickly to changes in energy requirements. This process of metabolizing substrate into ATP can be divided into a three stage process (as described by Jafri et al. Annu. Rev. Biomed. Eng. 2001 3:57–81). In the first stage, energy substrate is delivered across the mitochondrial inner membrane to the tricarboxylic acid (TCA or Krebs) cycle via glycolysis of carbohydrates, β-oxidation of fatty acids, and conversion of amino acids into pyruvate or TCA cycle intermediates. In the second stage, the TCA cycle in the mitochondrial matrix links glycolysis to oxidative phosphorylation (OxPhos) through decarboxylation of pyruvate to acetyl-coenzyme A (CoA) and the complete oxidation of acetyl-CoA to $CO_2$ (see FIG. 1) In the third stage, oxidative phosphorylation (OxPhos) oxidizes reducing equivalents produced by the TCA cycle via the electron transport chain as a means of establishing a large electrochemical proton gradient across the mitochondrial inner membrane (see FIG. 2 for schematic of the OxPhos system and the interrelationship to the TCA cycle). This proton motive force is subsequently used by ATP synthase to couple the flow of protons into the mitochondrial matrix with the phosphorylation of adenosine 5'-diphosphate (ADP) to form ATP.

During ischemia or hypoxia, normal oxidative metabolism is jeopardized, with the risk of cell injury and cell death increasing with increased duration of ischemia or hypoxia. Sudden occlusion of an artery results in oxygen deprivation to the region downstream of the occlusion. This is followed by physiological and metabolic changes that begin within seconds, with the following sequence of events known to occur in a well-studied model of coronary occlusion in dogs (Kloner et al. Circulation 2001 104:2981–2989).

As taught by Kloner et al. (Circulation 2001 104:2981–2989), after about 8 seconds of decreased arterial blood flow, the $O_2$ trapped in the tissue as oxyhemoglobin and oxymyoglobin has been consumed and energy metabolism shifts from aerobic or mitochondrial metabolism to anaerobic glycolysis. Effective contractions begin to decrease and finally stop, and the myocardium stretches, instead of shortening, with each systole. The membrane potential decreases and electrocardiogram (ECG) changes can be observed.

Kloner et al. (Circulation 2001 104:2981–2989) also teaches that the energy demands of myocytes greatly exceed the supply from anaerobic glycolysis and reserves of high-energy phosphate (HEP). Thus, tissue ATP and creatine phosphate decrease and ADP and inorganic phosphate and hydrogen ions begin to accumulate. Creatine phosphate, a major reserve source of HEP, decreases rapidly with 90% being exhausted after 30 seconds of ischemia. ATP levels decrease more slowly with approximately 20% to 25% of the ATP present at the onset of ischemia still being present late in the reversible phase of ischemia. Approximately 80% of the new HEP in zones of severe ischemia is produced by anaerobic glycolysis. Glucose-1-P from glycogenolysis serves as the substrate in anaerobic glycolysis since little glucose is present in the extracellular fluid. The process of anaerobic glycolysis generates 3 μmol HEP per μmol of glucose-1-P (Kloner et al. Circulation 2001 104:2981–2989).

After about 10 minutes of ischemia, intracellular pH decreases to 5.8–6.0, and the load of intracellular osmotically active particles, lactate, inorganic phosphate, creatine, etc, increases markedly (Kloner et al. Circulation 2001 104:2981–2989). Only a modest increase in intracellular $H_2O$ is observed, however, since relatively little $H_2O$ is available in the extracellular space of severely ischemic tissue. This edema can be viewed by transmission electron microscopy as an increase in the sarcoplasmic space.

The adenine nucleotide pool is also degraded as the ADP formed from the action of ATPases accumulates and the rephosphorylation of ADP to ATP via anaerobic glycolysis is slowed by acidosis and lactate and the diffusion of adenosine into the extracellular fluid. Various substances including bradykinin, opioids, norepinephrine, and angiotensin, are also released into the extracellular fluid during the first few minutes of ischemia. Like adenosine, these agents bind to receptors on myocytes and stimulate intracellular signaling system responses. These reactions occur quickly. For example, phosphorylase is activated only a few seconds after the onset of ischemia by the norepinephrine that is released from intramyocardial sympathetic nerve endings as a response to ischemia (Kloner et al. Circulation 2001 104:2981–2989).

Calcium is involved in, and is essential for, triggering contraction. Its balance is critical to the cell, however, as overload of $Ca^{2+}$ causes hypercontraction, precipitation of $Ca^{2+}$ phosphate in the mitochondria, and ultimately cell death. In the isolated perfused heart, late in the reversible phase of ischemia, intracellular ionic $Ca^{2+}$ rises slightly (Kloner et al. Circulation 2001 104:2981–2989). This has been difficult to confirm, however, in vivo.

Restoration of arterial flow, also known as reperfusion, to ischemic living myocardium results in restoration of aerobic metabolism and salvage of the ischemic myocytes (Kloner et al. Circulation 2001 104:2981–2989). Upon reperfusion, the tissue develops reactive hyperemia caused by a 400% to 600% increase in blood flow. This increased blood flow reaches a peak during the first 5 minutes of reperfusion and then declines to normal control levels over the next 10 to 15 minutes. Excess $O_2$-derived free radicals also appear during the first minute of reperfusion and peak approximately 4 to 7 minutes after the onset of reperfusion. Generalized mitochondrial and cell swelling can be observed via electron microscopy during this period. ECG changes observed during ischemia disappear after 1 to 2 minutes of arterial reperfusion and a large amount of ATP is produced via rephosphorylation of the ADP and AMP that accumulated while the tissue was ischemic. Lactate decreases to control levels and the pH of the tissue returns to normal levels approximately 0.5 to 2 minutes after reperfusion (Kloner et al. Circulation 2001 104:2981–2989).

Preconditioning (PC), a phenomenon which exists in all species examined, including humans, is a form of protection wherein a brief ischemic or hypoxic episode prevents or reduces the extent of cellular or organ damage, death and/or cellular dysfunction from subsequent prolonged ischemia. PC may also be recruited pharmacologically using agonists such as adenosine and diazoxide. PC may also occur from other events and/or agents causing cell death, damage and/or cellular dysfunction. Preconditioning occurs in various organs and tissues including, but not limited to, myocardium, skeletal muscle, smooth muscle, liver, brain and kidney.

For example, adenosine is released from cells immediately with ischemia and affects organs such as the heart as well as the vascular system through a second messenger signaling cascade triggered by binding to adenosine $A_1$, $A_{2a}$, $A_{2b}$ and/or $A_3$ receptors. In the heart, adenosine affects the intrinsic conducting system (bradycardia and AV block potential arrhythmia). In myocytes it affects the $Ca^{2+}$ current (negative inotropic) and has been proposed to influence the function of mitochondrial $K_{ATP}$ channels-. It can affect the vascular system as well causing vasodilation. Adenosine causes preconditioning, potentially through activation of protein kinase C (PKC) and modulation of the mitochondrial and/or sarcolemmal $K_{ATP}$ channel (Cohen et al. Annu Rev Physiol 2000 62:79–109), although the underlying mechanism remains controversial.

SUMMARY OF THE INVENTION

It has now been found that modifications to a number of proteins, including but not limited to, proteins involved in the TCA cycle, OxPhos pathways, $Ca^{2+}$ handling, and/or chaperoning as well as proteins selected from aldehyde dehydrogenase, NG-dimethylarginine dimethylaminohydrolase (DDAH) and the RNA binding protein regulatory subunit DJ-1, occur during pharmacological preconditioning, a treatment which mimics many aspects of classical ischemic preconditioning or hypoxia, including protection of a cell, tissue or organ from damage resulting from prolonged periods of ischemia, hypoxia, ischemia/reperfusion, hypoxia/reperfusion or any other event or agent that causes or promotes cell death (necrosis or apoptosis) or injury. These proteins, namely modified proteins of the TCA cycle, modified proteins of the OxPhos pathways, modified $Ca^{2+}$ handling proteins, modified chaperoning proteins and modified aldehyde dehydrogenase, modified NG-dimethylarginine dimethylaminohydrolase (DDAH) and modified RNA binding protein regulatory subunit DJ-1 are referred to herein as "preconditioning proteins".

Accordingly, an aspect of the present invention relates to methods for identifying new compositions, methods or events useful in modulating a preconditioning protein and/or in priming a cell for preconditioning and/or inducing preconditioning and/or modulating preconditioning of a cell, tissue or organ.

Another aspect of the present invention relates to methods for diagnosing and/or monitoring in a subject preconditioning and/or ischemic, hypoxic, ischemia/reperfusion and/or hypoxia/reperfusion conditions and/or the ability of a cell, tissue or organ to survive injury by monitoring modulation of a preconditioning protein in the subject. One or more of the preconditioning proteins may be detected in a sample of injured tissue as well as in a biological fluid such as, for example, blood, serum, plasma, urine, saliva, bile, mucus, semen or cerebrospinal fluid, obtained from the subject. Diagnosis of an ischemic, hypoxic, ischemia/reperfusion or hypoxia/reperfusion condition can also be performed by comparing levels of a preconditioning protein measured in a subject with levels of the same preconditioning protein in a control. Modifications, as described herein, in a preconditioning protein in the subject as compared to the control, are indicative of an ischemic, hypoxic, ischemia/reperfusion, or hypoxia/reperfusion condition in the subject. In addition, modifications to a preconditioning protein can be monitored in a subject to assess whether a cell, tissue or organ has been subjected to sufficient preconditioning or requires additional preconditioning for protection from cell, tissue or organ injury or death.

Another aspect of the present invention relates to a composition, a method or an event for modulating a preconditioning protein involved in the TCA cycle and/or an OxPhos pathway, and/or $Ca^{2+}$ handling and/or chaperoning and/or a preconditioning protein selected from aldehyde dehydrogenase, NG-dimethylarginine dimethylaminohydrolase (DDAH) and the RNA binding protein regulatory subunit DJ-1, in a cell, tissue or organ, said composition, method or event being one that induces preconditioning.

Yet another aspect of the present invention relates to a composition, method or event for priming a cell, tissue or organ for preconditioning and/or preconditioning a call tissue or organ and preventing injury and/or death and/or modulating preconditioning of a cell, tissue or organ by modulating a preconditioning protein.

BRIEF DESCRIPTION OF THE FIGURES

FIG. 5A shows a Coomassie stained gel of 400 μg of rabbit ventricular myocytes HEPES extract focused between pH 4–7 and resolved by 12.5% SDS-PAGE. FIG. 5B shows a silver stained gel of 200 μg of rabbit ventricular myocytes HEPES extract focused between pH 6–9 and resolved by 10% SDS-PAGE. Figure 5C shows a silver stained gel of 250 μg of rabbit ventricular myocytes HEPES extract focused between pH 3–10 and resolved by 12.5% SDS-PAGE. On each gel the protein spots are numbered. Table 1, infra, lists all proteins identified from the three 2-D gel separation methods, with the proteins numbered in accordance with the numbering of spots in the gel images.

DETAILED DESCRIPTION OF THE INVENTION

Figure 1:
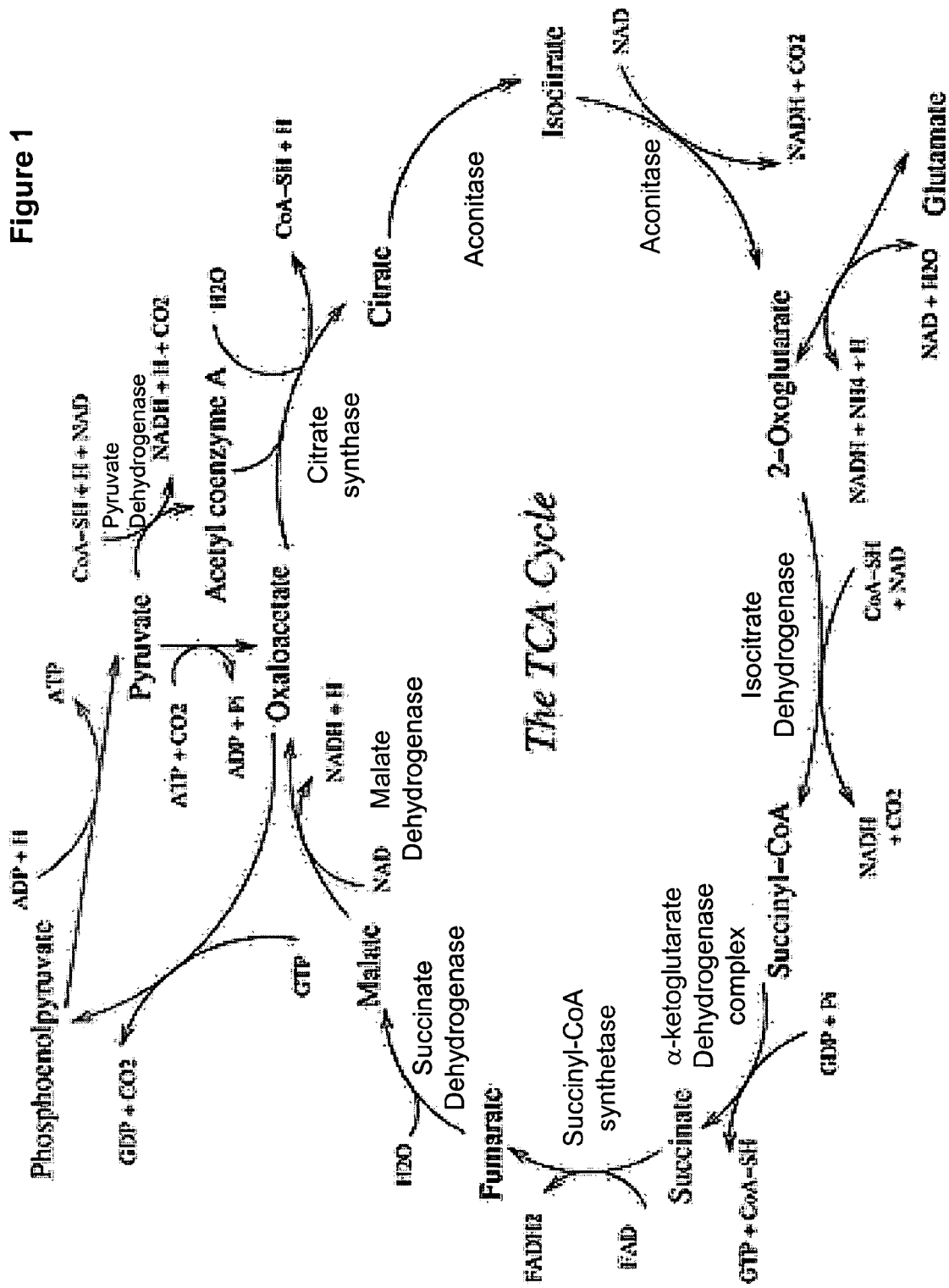
FIG. 1 is a schematic representation of the TCA cycle. This diagram shows all the intermediates, with the corresponding enzymes indicated that are responsible for converting between each of the intermediates. All of these processes occur within the mitochondrial matrix, and all enzymes are found within the matrix, except for succinate dehydrogenase, which is embedded in the inner mitochondrial membrane. Succinate dehydrogenase also functions as Complex II of the OxPhos system (described in FIG. 2). Another important enzymatic process associated with the TCA cycle that is not responsible for conversion between intermediates is that of pyruvate dehydrogenase, which converts pyruvate to acetyl CoA, the initial input substrate for TCA cycle functioning. Acetyl CoA entry is shown in the conversion of oxaloacetate to citrate, at the top of the figure.
Figure 2:
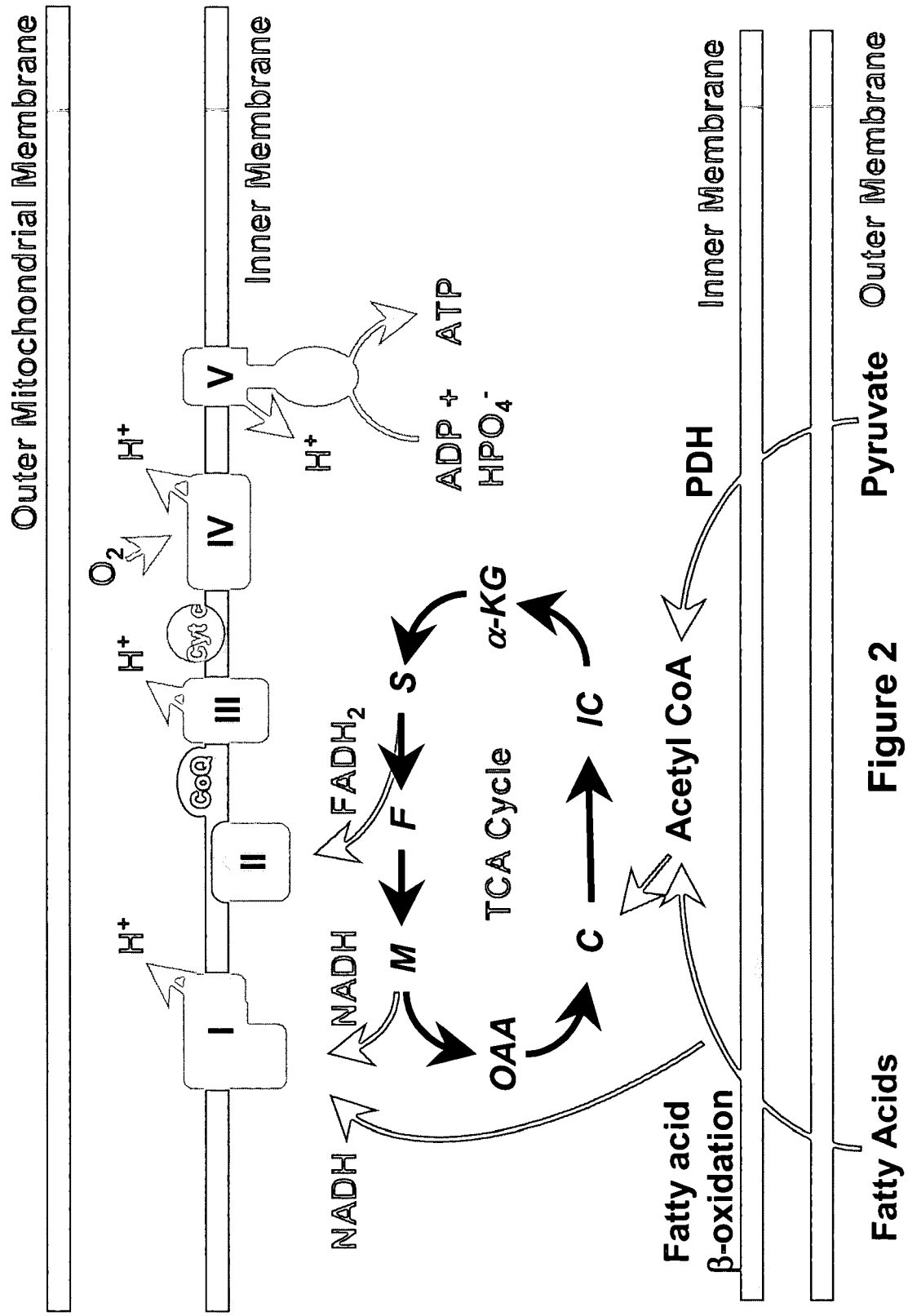
FIG. 2 is a schematic representation of the oxidative phosphorylation system complexes of the inner mitochondrial membrane showing their interrelationship to the TCA cycle. The schematic shows: (1) the two major sources of the TCA cycle substrate, acetyl CoA, derived from either fatty acid or pyruvate; (2) where acetyl CoA feeds into the TCA cycle and the reducing equivalents NADH and $FADH_2$ feed into OxPhos complexes I and II in order to facilitate the reduction of $O_2$ to $H_2O$; (3) the five protein complexes (I–V) that comprise the OxPhos system; and (4) the production of ATP that occurs from complex V as a result of both electron transport that initiates from either complex I or II, then proceeds through III and IV to fully reduce $O_2$ to $H_2O$, with the associated $H^+$ transport that occurs through complexes I, III, and IV. The outer and inner mitochondrial membranes are indicated, showing the position of the OxPhos complexes within the inner mitochondrial membrane. The OxPhos complexes labeled I–V are: (I) NADH ubiquinone oxidoreductase; (II) succinate dehydrogenase; (III) ubiquinone cytochrome c oxidoreductase; (IV) cytochrome c oxidase; and (V) ATP synthase. Other molecules are labeled as follows: CoQ is ubiquinone, cyt C is cytochrome c, and the TCA cycle intermediates are abbreviated for simplicity (C=citrate; IC=isocitrate; α-KG=α-ketoglutarate; S=succinate; F=fumarate; M=malate; OAA=oxaloacetate).

PC triggers two windows of protection, the first (classical PC) becoming manifest within 15 minutes and lasting 1–3 hours. The rapid onset and short duration of protection afforded by classical PC are likely the result of post-translational protein modifications, as 15 minutes is unlikely to be a sufficient time period to recruit significant de novo transcription and translation, and it has been shown that preconditioning can still be conferred in the presence of protein synthesis inhibitors (Thornton et al. Am. J. Physiol. 1990 259:H1822-5). A second, less effective window, known as late preconditioning, begins after 24 hours and lasts 24 to 72 hours. The effects of this second window have been ascribed to reactive oxygen species, de novo protein synthesis resulting from altered gene regulation and/or expression, and post-translational modifications (Bolli, R. Circ. Res. 2000 87:972–83). Regulation of protein processing and/or turnover may also be responsible for modulation and/or alteration of nascent and/or functional protein quantities in this second window.

Using a multi-tiered proteomic approach that relied on a sequential subproteomic fractionation, followed by resolution of proteins across a variety of pH gradients and protein loads (see the approach schematic, FIG. 3), a large number of significant protein modifications occurring during either adenosine or diazoxide preconditioning have now been identified (see FIG. 4). In particular, it has now been found that proteins of the TCA cycle and OxPhos and $Ca^{2+}$ handling pathways, chaperone proteins and proteins selected from aldehyde dehydrogenase, NG-dimethylarginine dimethylaminohydrolase (DDAH) and the RNA binding protein regulatory subunit DJ-1 are modified during preconditioning. These protein modifications are believed to underlie the beneficial effects on organs of preconditioning. These modified proteins may provide for protection of cells against an ischemic or hypoxic event or may prime the cell to protect itself from an ischemic or hypoxic event.

By "prime" or "priming" as used herein it is meant that the modification to the protein leads to or results in: (1) a change via cross-talking, a feed-back mechanism and/or a signaling mechanism which ultimately effects the first window of preconditioning, the second window of preconditioning or both windows of preconditioning of a cell; or (2) a change in function of the protein complex or pathway of which the modified protein is a member. For example, the protein may be a subunit of an enzyme that has had its function altered, without necessarily showing a change in cross-talk, feed-back, or signaling as described above.

By "preconditioning protein" as used herein it is meant a protein whose modification is observed during or following preconditioning. Exemplary preconditioning proteins identified herein are preferably modified mitochondrial proteins. More preferably the preconditioning protein is involved in $Ca^{2+}$ handling, the TCA cycle, chaperoning, and/or the OxPhos pathway or is a protein selected from aldehyde dehydrogenase, NG-dimethylarginine dimethylaminohydrolase (DDAH) or the RNA binding protein regulatory subunit DJ-1. Use of the term "protein" herein, is meant to include full length proteins as well as fragments of the proteins, including but not limited to degradation products, precursors, subunits of proteins and post-translationally modified forms of the proteins.

The present invention provides compositions and methods or events for modulating these preconditioning proteins, priming a cell for preconditioning and/or inducing or modulating preconditioning in a cell, tissue or organ. The present invention also provides methods for identifying new compositions or events capable of modulating these preconditioning proteins, priming a cell for preconditioning and/or inducing or modulating preconditioning in a cell, tissue or organ. In addition, the present invention provides methods for diagnosing and monitoring preconditioning and/or ischemic, hypoxic, ischemia/reperfusion or hypoxia/reperfusion conditions and/or the ability of a cell, tissue or organ to survive injury in a subject based upon detection of one or more of these preconditioning proteins.

For purposes of the present invention, by the term "preconditioning" or "PC" as used herein is meant to be inclusive of ischemic, hypoxic, and/or pharmacological preconditioning, as well as preconditioning recruited by other events and/or agents causing cell death (necrosis or apoptosis), damage and/or dysfunction.

By the term "event" as used herein, it is meant an incident or experience of a cell, tissue or organ resulting in the preconditioning protein modifications observed herein. Examples of such events include, but are in no way limited to, hypoxia, ischemia, glucose deprivation, thermal shock (high or low), alcohol consumption, hemorrhaging, dehydration and sepsis.

By the phrase "protein modification" or "protein modifications" as used herein, it is meant to include changes, in particular increases or decreases in relative protein abundance, as well as changes in type or abundance or direction of post-translational modifications or other chemical adducts. By "post-translationally modified" or "post-translational modification" it is meant to be inclusive not only of phosphorylation of amino acid residues, but also of other chemical adducts. Chemical adducts known in the art relating to post-translational modification of proteins include, but are not limited to, phosphorylation, glycosylation, glycation, myristylation, prenylation, phenylation, acetylation, nitrosylation, oxidation, s-glutathiolation, amidation, biotinylation, c-mannosylation, flavinylation, farnesylation, formylation, geranyl-geranylation, hydroxylation, lipoylation, methylation, palmitoylation, sulphation, gamma-carboxyglutamic acids, N-acyl diglyceride (tripalmitate), O-GlcNAc, pyridoxal phosphate, phospho-pantetheine, pyrrolidone carboxylic acid, ribosylation and ADP-ribosylation. Preferred chemical adducts are phosphorylation, oxidation, glycosylation, myristylation, prenylation, acetylation, nitrosylation, sulphation, ribosylation and ADP-ribosylation. Thus, by "post-translationally modified" it is meant to be inclusive of any of the above chemical adducts and/or any combination thereof to mature proteins as well as precursors and subunits thereof. Chemical adducts of preconditioning proteins include such post-translational modification of intact preconditioning proteins and of degradation products of preconditioning proteins.

The phrase "degradation product" is defined as any fragment of a preconditioning protein. Degradation products can be produced by, for example proteolysis.

By the term "modulate", "modulates" or "modulating" as used herein, it is meant a change, i.e. an increase or decrease in the level of a protein identified herein and/or an increase or decrease in the level of a post-translationally modified form of a protein identified herein, and/or a different type of post-translational modification to a protein identified herein, and/or a change in partitioning of a protein or proteins in the cell.

Protein modifications occurring during preconditioning were identified by a multi-tiered two-dimensional gel electrophoresis approach (see FIG. 3) and subsequent analysis of the cytoplasmic and TFA extracts of adenosine and diazoxide-treated isolated cardiomyocytes (n=4) at concentrations capable of invoking preconditioning. This analysis revealed modifications to pathways of oxidative metabolism involving primarily proteins of the TCA cycle, the electron transport chain responsible for OxPhos and energy production (in the form of ATP) within the mitochondria of the cell, $Ca^{2+}$ handling proteins and chaperoning proteins as well as proteins selected from aldehyde dehydrogenase, NG-dimethylarginine dimethylaminohydrolase (DDAH) and the RNA binding protein regulatory subunit DJ-1 (FIG. 4). The modified proteins identified herein are referred to as preconditioning proteins.

Preconditioning proteins of the TCA cycle identified as modified include isocitrate dehydrogenase NAD+ specific subunit alpha (IDH), dihydrolipoamide succinyltransferase, succinyl CoA ligase [ADP forming] beta chain and protein X (also known as E3 binding protein, of the pyruvate dehydrogenase (PDH) complex) (FIG. 4). PDH is an indirect component of the TCA cycle, since it is responsible for formation of acetyl CoA, which is the substrate that feeds into and is essential for TCA cycle functioning. In particular, pharmacological preconditioning with diazoxide resulted in increases in IDH and post-translational modification of protein X, and a decrease in dihydrolipoamide succinyltransferase. Pharmacological preconditioning with adenosine resulted in an increase of IDH and succinyl CoA ligase [ADP forming] beta chain. It is believed that aconitate hydratase (aconitase), another TCA cycle subunit, may also be a preconditioning protein undergoing changes in post-translation modification during preconditioning.

Preconditioning proteins of the oxidative phosphorylation (OxPhos) system that were modified (see FIG. 4) include proteins within Complex I (NADH ubiquinone oxidoreductase), Complex III (ubiquinol cytochrome c oxidoreductase), and Complex V ($F_1F_0$ ATPase or ATP synthase). In particular, pharmacological preconditioning with diazoxide increased the 23 kDa, 24 kDa, and 30 kDa subunits (mitochondrial precursors) of Complex I, decreased core protein I of Complex III, and in Complex V, it increased the δ chain (mitochondrial precursor) of the $F_1$ portion, and increased the d chain (mitochondrial precursor) of the $F_0$ portion. Pharmacological preconditioning with adenosine also decreased core protein I of Complex III and caused increases in the δ chain (mitochondrial precursor) of the $F_1$ portion, and in the 24 kDa and 30 kDa subunits, (mitochondrial precursors) of Complex I. Also, adenosine induced an increase in the extent of post-translational modification of the β chain of $F_1$ portion (mitochondrial precursor) of Complex V. The increase in post-translational modification was detected by the presence of two additional spots at the molecular weight of the intact protein, but which are more acidic, in adenosine-treated myocytes subjected to isoelectric focusing in the first dimension and SDS-PAGE in the second dimension, followed by silver stain or western blot analysis. In contrast, identical extracts from control samples had only a single protein spot.

In addition to the TCA cycle and OxPhos protein changes, two chaperone proteins involved in either mitochondrial protein transport or protein complex assembly were also modified by preconditioning (see FIG. 4).

One chaperone protein that was modified by both adenosine and diazoxide was metaxin 2, which was found to be reduced in cell extracts treated with either drug. Metaxin 2 is one subunit of a protein complex responsible for the transport of proteins across the outer mitochondrial membrane (Armstrong et al. J Cell Biochem 1999 74:11–22). The vast majority of mitochondrial proteins are encoded by the nuclear genome, and following synthesis outside the mitochondria, they must traverse the mitochondrial membranes prior to reaching their final destinations either within the mitochondrial matrix or the inner mitochondrial membrane, as is the case for many of the OxPhos subunits. Metaxin 2 is one of many chaperones that assist in this translocation process.

Another chaperone protein, prohibitin, was modified by adenosine preconditioning. Rather than acting as a transport chaperone, this protein is known to function at the surface of the inner mitochondrial membrane in the intermembrane space (Back et al. Protein Sci. 2002 11:2471–2478), as part of a protein complex that functions in the assembly of mitochondrial respiratory chain (OxPhos) complexes. It does so by binding to and stabilizing newly synthesized mitochondrial subunits against degradation by mitochondrial membrane bound metalloproteases during transport and assembly in the inner mitochondrial membrane (as reviewed by Nijtmans et al. Cell Mol Life Sci 2002 59:143–155). Furthermore, it has been suggested that prohibitin function is specifically required in situations of metabolic stress (Nijtmans et al. EMBO J. 2000 19:2444–2451).

Also modified during preconditioning are proteins involved in $Ca^{2+}$ handling or mobilization from the sarcoplasmic reticulum (SR). The SR is a modified endoplasmic reticulum consisting of interconnecting sacs and tubes surrounding the myofibrils (contractile proteins) that contain/store large amounts of $Ca^{2+}$, which can be released into the cytoplasm to trigger muscle contraction in a process known as $Ca^{2+}$-induced $Ca^{2+}$ release (CICR). CICR occurs when a small amount of extracellular $Ca^{2+}$ enters the myocyte, which then triggers a large amount of $Ca^{2+}$ release from the SR through the $Ca^{2+}$ release channel, also called ryanodine receptor. Besides the importance for muscle contraction, $Ca^{2+}$ mobilization is important for $Ca^{2+}$-dependent cellular signaling, and for $Ca^{2+}$-dependent activation of three TCA cycle dehydrogenases (IDH, PDH, and α-ketoglutarate dehydrogenase).

One $Ca^{2+}$ handling protein modified by preconditioning was the 58 kDa isoform of sarcalumenin, which is present in the SR (see FIG. 4). Phosphorylation of cardiac sarcalumenin prevents its binding to the ryanodine receptor (as determined by Hadad et al. J Memb Biol. 1999 170(1):39–49). Thus, it is believed that sarcalumenin plays a role in CICR by regulating ryanodine receptor activity. Sarcalumenin is also present in skeletal muscle where its quantity is affected by chronic low frequency stimulation and hibernation. A decrease in sarcalumenin levels is observed in the HEPES extract of cells preconditioned with diazoxide. This reduction may result from a variety of factors, for instance, a change in phosphorylation state that gives sarcalumenin different affinity for the ryanodine receptor in the presence of diazoxide, or it may simply indicate a difference in absolute quantity arising via differences in extent of protein degradation.

Another protein with an influence on $Ca^{2+}$ mobilization, ADP ribosyl hydrolase, was modified by both adenosine and diazoxide preconditioning (see FIG. 4). This protein, which was increased in drug treated extracts relative to matching control extracts, mediates the removal of ADP ribose moieties from proteins post-translationally modified by ADP ribosylation (as reviewed by Higashida et al. Pharmacology & Therapeutics 2001 90:283–296). The importance of ADP ribosyl hydrolase during preconditioning may relate to one or both of two factors, $Ca^{2+}$ handling and OxPhos Complex I activity, each of which may arise due to their association with metabolism of intracellular nicotinamide adenine dinucleotide ($NAD^+$).

As reviewed by Higashida et al. (Pharmacology & Therapeutics 2001 90:283–296), $NAD^+$ metabolism involves a large number of enzymes, one of which is ADP ribosyl hydrolase. One of the major products of $NAD^+$ metabolism is cyclic ADP ribose (cADPR), which can regulate $Ca^{2+}$ release from the ryanodine receptor, and in particular Type II ryanodine receptors, either by direct interaction with the receptor, or by interacting with FK506, another protein that regulates ryanodine receptor activity (as taught to us by Higashida et al. Pharmacology & Therapeutics 2001 90:283–296). Formation of ADP ribose by ADP ribosyl hydrolase promotes the formation of cADPR from $NAD^+$ by inhibiting another enzyme, cADPR hydrolase, thereby influencing $Ca^{2+}$ release from the SR (Genazzani et al. Biochem Biophys Res Commun 1996 223:502–507).

Besides the influence on cADPR and SR $Ca^{2+}$ release, ADP ribosyl hydrolase can also influence functioning of the OxPhos system. Complex I of the OxPhos system functions by using NAD+ as a source of reducing equivalents to initiate a series of oxidation reduction reactions that drive electron transport through the OxPhos system. The significance of ADP ribosyl hydrolase to this process is that the formation of ADP ribose, the by-product of ADP ribosyl hydrolase activity, has been shown to competitively inhibit OxPhos Complex I activity (Zharova and Vinogradov, Biochim Biophys Acta 1997 1320:256–264).

Another possibility of the effect of ADP ribosyl hydrolase on $Ca^{2+}$ mobilization is that it may influence release of $Ca^{2+}$ not from the SR, but from mitochondria themselves, via the influence ADP ribosyl hydrolase has on increasing the abundance of cADPR. As taught by Ziegler (Eur. J. Biochem. 2000 267:1550–1564), cADPR may stimulate the release of $Ca^{2+}$ from mitochondria. Since one of the proposed mechanisms of cell death is by precipitation of $Ca^{2+}$ phosphate in the mitochondria, prevention of mitochondrial $Ca^{2+}$ overload by cADPR may participate in prevention of cell death.

Four additional proteins were also found to be modified by preconditioning (see FIG. 4). One of the proteins, previously linked to preconditioning, is HSP27. Dana et al (Circ Res 2000;86:989–997) demonstrated that the preconditioning effect of activating adenosine A1 receptors was accompanied by phosphorylation of HSP27, which is believed to enhance its protective effect. We did not, however, observe a change upon administration of adenosine, but did see an increase following diazoxide treatment.

The other proteins, NG-dimethylarginine dimethylaminohydrolase (DDAH), an RNA binding protein regulatory subunit, also known as DJ-1, and aldehyde dehydrogenase have not previously been linked to preconditioning. All of these proteins were increased in diazoxide-treated cells, while only DJ-1 and aldehyde dehydrogenase increased following treatment with adenosine. DDAH was decreases following treatment with adenosine.

DJ-1 has been taught to be converted into a variant having a more acidic pI in response to exogenous oxidative stress or endogenous reactive oxygen species (Bonifati et al. J Mol Med. 2004 82:163–174), suggesting a role for DJ-1 as an antioxidant, or a sensor of oxidative stress. The changes observed during adenosine and diazoxide preconditioning may relate to this pI shift, or may relate to proposed functions of the protein. Although these are still not well understood, Bonifati et al. (J Mol Med. 2004 82:163–174) have proposed that DJ-1 is involved in cellular stress responses at three possible levels: (1) it may directly react to stress signals (e.g., redox changes, misfolded proteins) being an antioxidant and/or a molecular chaperone; (2) it may modulate gene expression of the stress response at the post-transcriptional level by its known interaction with RNA-binding protein complexes; and (3) it may translocate to the nucleus in response to stress signals, and in so doing, modulate gene expression directly at the transcriptional level.

DDAH is the only protein identified herein which is affected by both diazoxide and adenosine preconditioning that is modified in different directions by the two agents, being increased by diazoxide and decreased by adenosine treatment. This enzyme metabolizes asymmetric dimethylarginine, which is an endogenous inhibitor or nitric oxide synthase (NOS), thereby facilitating the synthesis of nitric oxide. Dayoub et al. (Circulation. 2003 108:3042–3047) demonstrated that DDAH overexpression in transgenic mice increases NOS activity in vitro and in vivo, leading to physiological effects consistent with increased production of nitric oxide, such as reduced systolic blood pressure, systemic vascular resistance, and cardiac stroke volume. This indicates that metabolism of endogenous asymmetric dimethylarginine plays an important role in regulation of NOS activity, and both nitric oxide and NOS activity are important factors in the late phase of preconditioning, as taught by Dawn and Bolli (Ann NY Acad Sci. 2002 962:18–41).

Figure 5A:
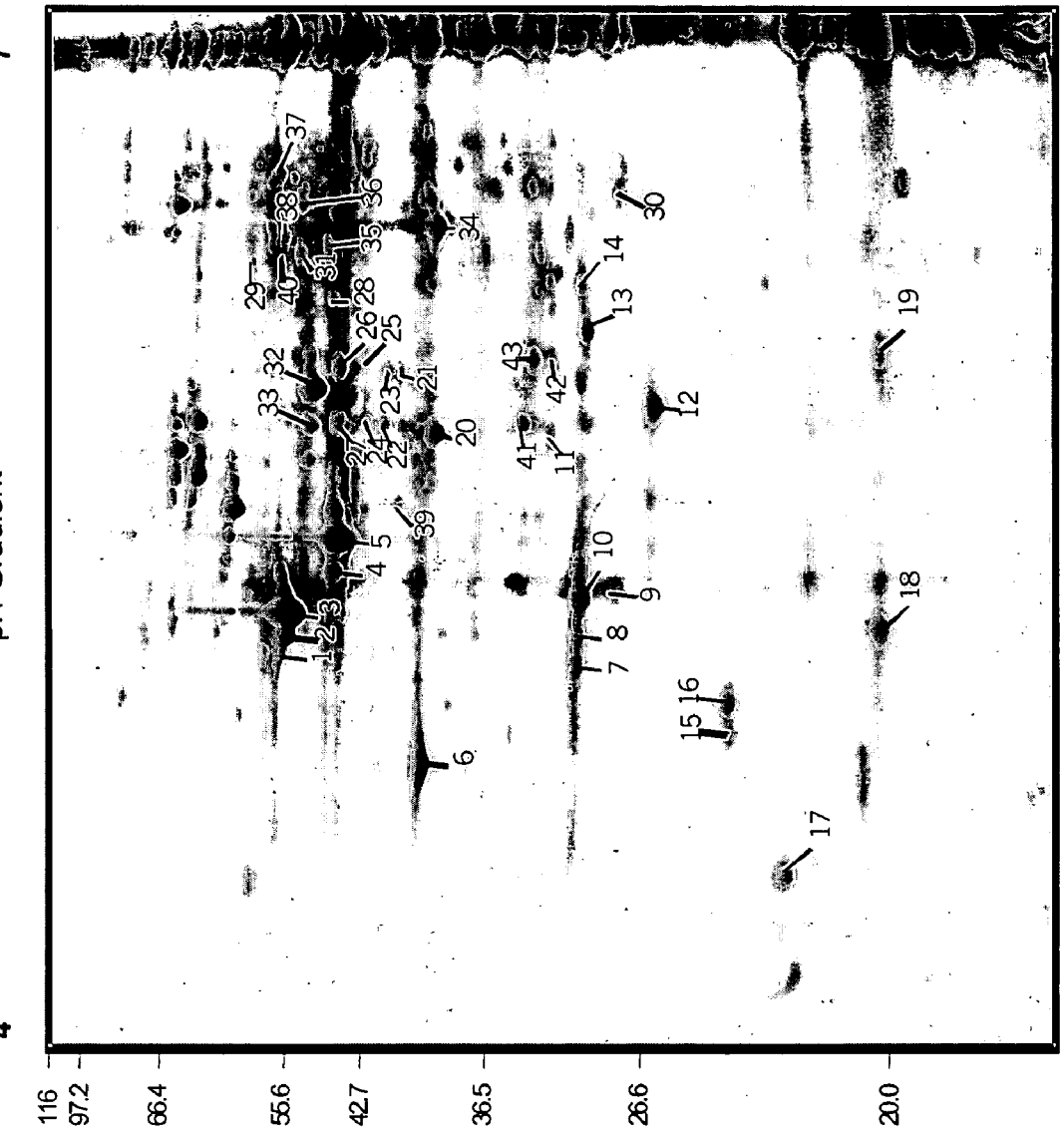
FIGS. 5A through 5C are gels showing the position of all proteins identified, including ones that do change and ones that do not, in the process of analysis for proteomic modifications by either adenosine or diazoxide preconditioning.
Figure 5B:
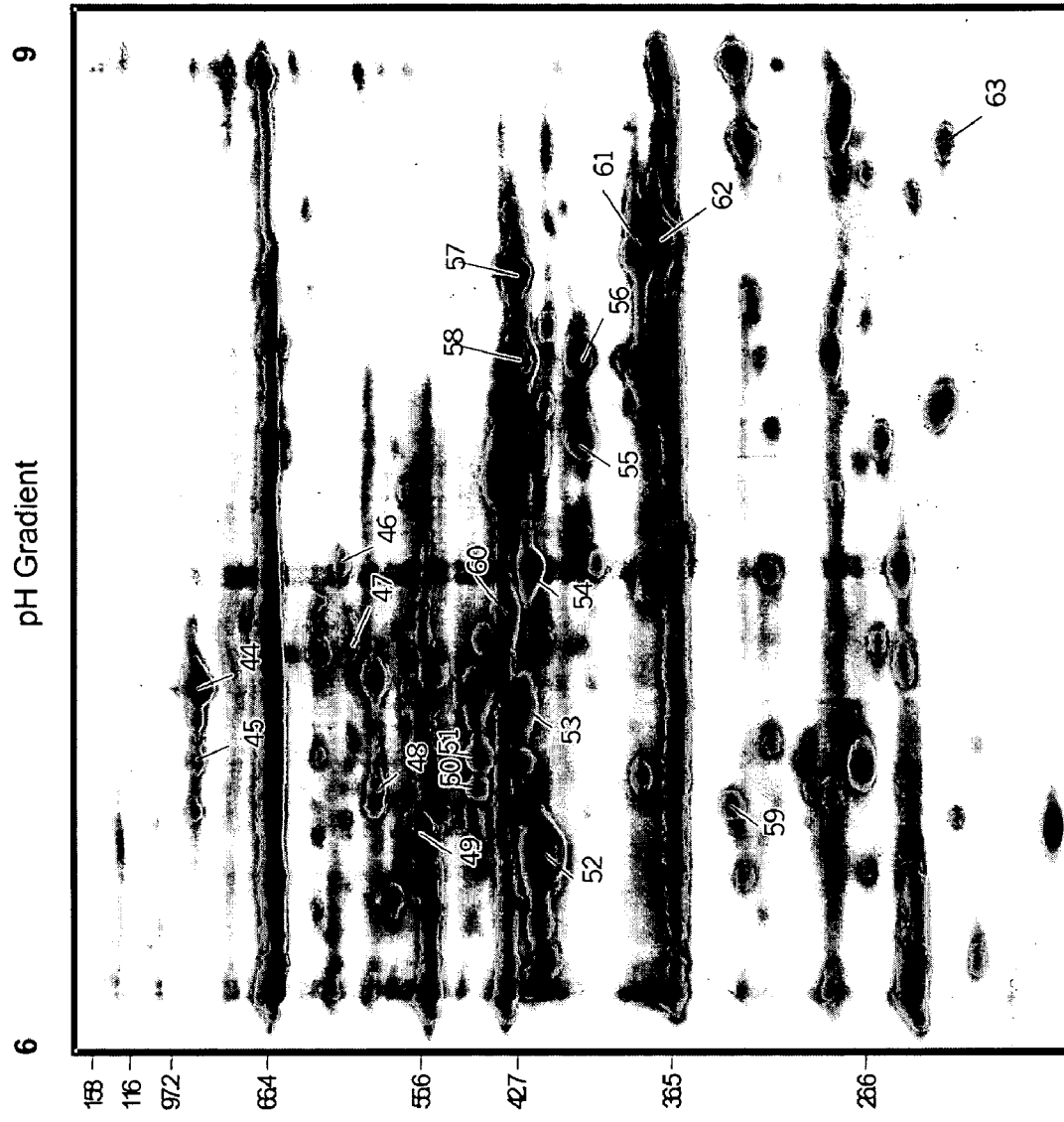
Figure 5C:
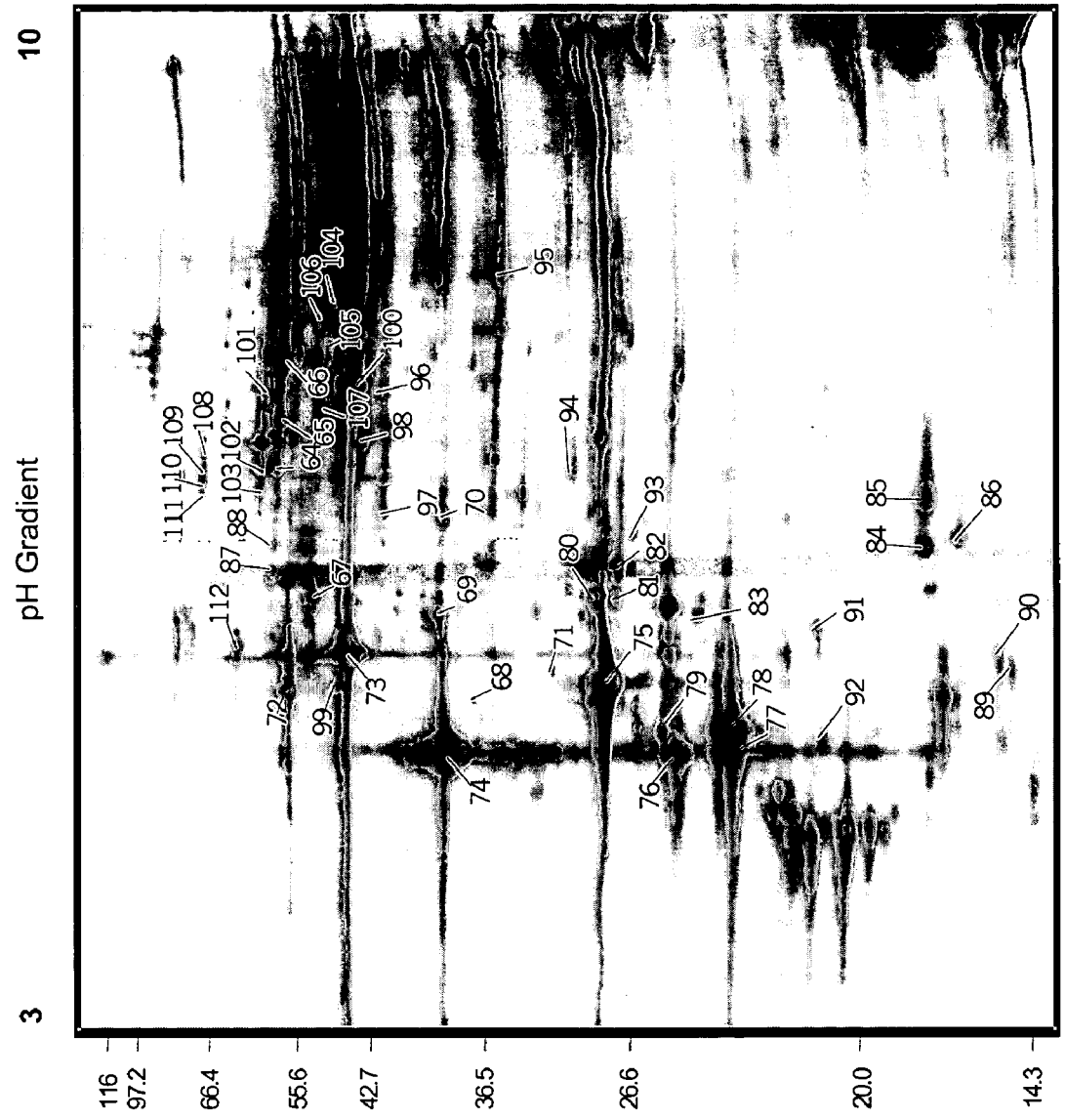

While many protein modifications by each preconditioning agent were detected and identified, these were by no means all the proteins identified during this study. A total of 112 individual protein spots taken from gels resolved under 3 distinct conditions were identified (FIG. 5 and Table 1).

TABLE 1

Protein species identified by MALDI and MS/MS. Numbers 1–43 correspond to the gel in FIG. 5A, numbers 44–63 correspond to the gel in FIG. 5B, and numbers 64–112 correspond to the gel in FIG. 5C. Proteins existing as multiple species in a gel are indicated by *, while species detected in more than one gel map are indicated by ‡.

| Spot # | Name | Identified by: | % coverage, # of peptides sequenced | Accession # | Function |
|---|---|---|---|---|---|
| 1*‡ | ATP synthase beta chain | MALDI | 50 | P10719 | ATP production, oxidative phosphorylation |
| 2*‡ | | | 54 | | |
| 3*‡ | | | 60 | | |
| 4*‡ | Alpha-actin, cardiac | MALDI | 60 | P04270 | Myocyte structure, muscle contraction |
| 5*‡ | | | 68 | | |
| 6‡ | Tropomyosin, alpha chain | MALDI | 45 | P09493 | muscle contraction |
| 7*‡ | Myosin light chain 1 | MALDI | 62 | P08590 | |
| 8*‡ | | | 58 | | |
| 9 | NADH oxidoreductase 23 kDa subunit | MALDI | 43 | P42028 | ATP production, oxidative phosphorylation |
| 10*‡ | Myosin light chain 1 | MALDI | 2 peptides | P08590 | muscle contraction |
| 11‡ | Heat shock protein 27 | MS/MS | 5 peptides | P42929 | Stress response |
| 12 | ATP synthase subunit d | MS/MS | 2 peptides | Q9DCX2 | ATP production, Oxidative phosphorylation |
| 13 | Thioredoxin-dependent peroxide reductase | MS/MS | 2 peptides | Q06830 | Free radical metabolism |
| 14‡ | NADH ubiquinone oxidoreductase 24 kDa subunit | MALDI | 35 | Q9D6J6 | ATP production, Oxidative phosphorylation |
| 15*‡ | Myosin light chain 2 (ventricular/cardiac isoform) | MALDI | 60 | P51667 | muscle contraction |
| 16*‡ | | | 48 | | |
| 17 | ATP synthase delta chain | MS/MS | 5 peptides | P30049 | ATP production, |
| 18 | Cytochrome c oxidase polypeptide Va | MALDI | 85 | P00426 | Oxidative phosphorylation |
| 19 | Fatty acid binding protein | MALDI | 70 | P10790 | Intracellular transport of fatty acids |

TABLE 1-continued

Protein species identified by MALDI and MS/MS. Numbers 1–43 correspond to the gel in FIG. 5A, numbers 44–63 correspond to the gel in FIG. 5B, and numbers 64–112 correspond to the gel in FIG. 5C. Proteins existing as multiple species in a gel are indicated by *, while species detected in more than one gel map are indicated by ‡.

| Spot # | Name | Identified by: | % coverage, # of peptides sequenced | Accession # | Function |
|---|---|---|---|---|---|
| 20‡ | Pyruvate dehydrogenase E1 beta subunit | MALDI | 36 | P11177 | Glycolysis, ATP production |
| 21 | NG, NG - dimethylarginine dimethylaminohydrolase | MALDI, MS/MS | 30, 2 peptides | O94760 | Amino acid modification, NO synthase regulation |
| 22* | Isocitrate dehydrogenase subunit alpha NAD+ specific | MALDI | 37 | P50213 | TCA acid cycle, ATP production |
| 23* | | | 37 | | |
| 24* | ADP-ribosyl hydrolase | MS/MS | 2 peptides | Q8NDY3 | ADP-ribose modulation - cell signaling |
| 25* | | | 2 peptides | | |
| 26 | Succinyl-CoA ligase [ADP forming] beta chain | MALDI | 25 | O97580 | TCA acid cycle, ATP production |
| 27 | Succinyl-CoA ligase [GDP-forming] beta chain | MALDI, MS/MS | 27, 3 peptides | Q96I99 | |
| 28* | Dihydrolipoamide succinyl transferase | MS/MS | 5 peptides | P11179 | |
| 29 | Protein disulfide isomerase A3 | MS/MS | 5 peptides | P30101 | Disulfide bond generation/breakdown |
| 30 | RNA-binding regulatory subunit (identical to DJ-1) | MS/MS | | O14805 (Q99497) | Transcriptional modulation |
| 31* | Dihydrolipoamide succinyl transferase | MS/MS | 3 peptides | P11179 | TCA acid cycle, ATP production |
| 32*‡ | Ubiquinol cytochrome c reductase core protein I | MS/MS | 5 peptides | P31930 | Oxidative phosphorylation, ATP production |
| 33*‡ | | | 5 peptides | | |
| 34‡ | L-lactate dehydrogenase beta chain | MALDI | 35 | P07195 | Glycolysis, ATP production |
| 35 | NADH oxidoreductase 49 kDa subunit | MALDI | 40 | P17694 | Oxidative phosphorylation, ATP production |
| 36* | Dihydrolipoamide succinyl transferase | MS/MS | 12 peptides | P11179 | TCA acid cycle, ATP production |
| 37 | Sarcalumenin, 58 kDa isoform | MALDI | 20 | P13666 | Possible role in ryanodine receptor regulation |
| 38 | Aldehyde dehydrogenase | MALDI, MS/MS | 19, 10 peptides | P11884 | Aldehyde metabolism |
| 39 | 2-oxoisovalerate dehydrogenase beta subunit | MS/MS | 3 peptides | P21953 | TCA acid cycle, ATP production |
| 40*‡ | Pyruvate dehydrogenase E3 binding protein | MS/MS | 5 peptides | O00330 | Glycolysis, ATP production |
| 41 | Prohibitin | MALDI | 69 | P35232 | Mitochondrial protein complex assembly |
| 42 | Metaxin 2 | MALDI | 31 | O88441 | Mitochondrial protein transport |
| 43 | NADH ubiquinone oxidoreductase 30 kDa subunit | MALDI | 44 | P23709 | Oxidative phosphorylation, ATP production |
| 44* | Aconitate hydratase | MALDI | 37 | P16276 | ATP production, TCA acid cycle |
| 45* | | | 30 | | |
| 46* | Pyruvate kinase M1 isozyme | MALDI | 31 | P11974 | ATP production, glycolysis |
| 47* | | | 47 | | |
| 48 | Glucose-6-phosphate isomerase | MALDI | 34 | Q9N1E2 | |
| 49‡ | ATP synthase alpha chain | MALDI | 55 | P25705 | ATP production, oxidative phosphorylation |
| 50*‡ | Fumarate hydratase | MALDI | 16 | P07954 | ATP production, TCA acid cycle |
| 51*‡ | | | 22 | | |
| 52 | Creatine kinase M chain | MALDI | 60 | P00563 | ATP regeneration |
| 53 | Citrate synthase | MALDI | 26 | O75390 | ATP production, TCA acid cycle |
| 54 | Creatine kinase, sarcomeric mitochondrial | MALDI | 65 | P17540 | ATP regeneration |
| 55* | Fructose bisphosphate aldolase A | MALDI | 67 | P00883 | ATP production, TCA acid cycle |
| 56* | | | 70 | | |

TABLE 1-continued

Protein species identified by MALDI and MS/MS. Numbers 1–43 correspond to the gel in FIG. 5A, numbers 44–63 correspond to the gel in FIG. 5B, and numbers 64–112 correspond to the gel in FIG. 5C. Proteins existing as multiple species in a gel are indicated by *, while species detected in more than one gel map are indicated by ‡.

| Spot # | Name | Identified by: | % coverage, # of peptides sequenced | Accession # | Function |
|---|---|---|---|---|---|
| 57* | Isocitrate dehydrogenase [NADP], mitochondrial | MALDI | 43 | Q04467 | |
| 58* | | | 42 | | |
| 59 | Triosephosphate isomerase | MALDI | 41 | P00939 | Glycolysis |
| 60 | Guanylate cyclase alpha-2 chain | MALDI | 16 | Q9WVI4 | Cell signaling |
| 61 | Malate dehydrogenase | MALDI | 41 | P08249 | ATP production, TCA acid cycle |
| 62 | Glyceraldehyde 3-phosphate dehydrogenase | MALDI | 48 | P46406 | ATP production, glycolysis |
| 63 | Adenylate kinase Isoenzyme 1 | MALDI | 55 | P00569 | ATP/ADP balance |
| 64*‡ | ATP synthase alpha chain | MALDI | 51 | P19483 | ATP production, oxidative phosphorylation |
| 65*‡ | | | 51 | | |
| 66*‡ | | | 40 | | |
| 67‡ | Ubiquinol-cytochrome C reductase complex core protein I | MALDI | 34 | P31930 | |
| 68*‡ | ATP synthase beta chain | MALDI | 50 | P10719 | |
| 69‡ | Pyruvate dehydrogenase E1 subunit | MALDI | 34 | P11177 | ATP production, glycolysis |
| 70‡ | L-lactate dehydrogenase beta chain | MALDI | 35 | P07195 | |
| 71*‡ | ATP synthase beta chain | MALDI | 33 | P10719 | ATP production, oxidative phosphorylation |
| 72*‡ | | | 48 | | |
| 73‡ | Alpha actin, cardiac | MALDI | 54 | P04270 | Muscle contraction |
| 74‡ | Tropomyosin, alpha chain | MALDI | 43 | P09493 | |
| 75*‡ | Myosin light chain 1 | MALDI | 70 | P08590 | |
| 76*‡ | | MALDI | 62 | | |
| 77*‡ | Myosin light chain 2 | MALDI | 51 | P10916 | |
| 78*‡ | | MALDI | 57 | | |
| 79*‡ | Myosin light chain 1 | MALDI | 59 | P08590 | |
| 80*‡ | | MALDI | 41 | P08590 | |
| 81*‡ | NADH ubiquinone oxidoreductase 24 kDa subunit | MALDI | 31 | P19404 | ATP production, oxidative phosphorylation |
| 82*‡ | | | 52 | | |
| 83*‡ | Myosin light chain 1 | MALDI | 58 | P08590 | Muscle contraction |
| 84 | Cytochrome c oxidase Vb | MS/MS | | P10606 | ATP production, oxidative phosphorylation |
| 85 | Cytochrome c oxidase VIa | MS/MS | | Q02221 | |
| 86 | NADH ubiquinone oxidoreductase 13 kDa subunit | MS/MS | | O75380 | ATP production, oxidative phosphorylation |
| 87*‡ | Pyruvate dehydrogenase E-3 binding protein | MS/MS | | O00330 | ATP production, glycolysis |
| 88*‡ | | MS/MS | | | |
| 89*‡ | Myosin light chain 2 | MALDI | 18 | P10916 | Muscle contraction |
| 90*‡ | | | 16 | | |
| 91*‡ | Myosin light chain 1 | MS/MS | | P08590 | |
| 92*‡ | Myosin light chain 1 | MALDI | 59 | P08590 | |
| 93 | Alpha-crystallin B chain | MALDI | 44 | P23927 | Organizational chaperone |
| 94 | Enoyl-CoA hydratase | MALDI | 23 | P14604 | ATP production, beta oxidation |
| 95 | D-beta-hydroxybutyrate dehydrogenase | MALDI | 28 | P29147 | ATP production, oxidative phosphorylation |
| 96 | Troponin T, cardiac | MALDI | 18 | P50751 | Muscle contraction |
| 97 | Acyl-CoA dehydrogenase, short chain specific | MALDI | 18 | P15651 | ATP production, beta-oxidation |
| 98 | Acyl-CoA dehydrogenase, long chain specific | MALDI | 22 | P15650 | ATP production, beta-oxidation |
| 99*‡ | ATP synthase beta chain | MALDI | 49 | P10719 | ATP production, oxidative phosphorylation |
| 100 | Creatine kinase M chain | MALDI | 47 | P00563 | ATP regeneration |
| 101 | Succinyl-CoA: 3 ketoacid coenzyme A transferase | MALDI | 20 | P55809 | ketone body catabolism |
| 102* | Dihydrolipoamide dehydrogenase | MALDI | 45 | P49819 | ATP production, the TCA acid cycle |
| 103* | | | 18 | | |

TABLE 1-continued

Protein species identified by MALDI and MS/MS. Numbers 1–43 correspond to the gel in FIG. 5A, numbers 44–63 correspond to the gel in FIG. 5B, and numbers 64–112 correspond to the gel in FIG. 5C. Proteins existing as multiple species in a gel are indicated by *, while species detected in more than one gel map are indicated by ‡.

| Spot # | Name | Identified by: | % coverage, # of peptides sequenced | Accession # | Function |
|---|---|---|---|---|---|
| 104*‡ | Fumarate hydratase | MALDI | 31 | P07954 | |
| 105*‡ | | | 28 | | |
| 106 | Beta enolase | MALDI | 18 | P25704 | ATP production, glycolysis |
| 107*‡ | Fumarate hydratase | MALDI | 15 | P07954 | ATP production, the TCA acid cycle |
| 108* | Succinate dehydrogenase [ubiquinone] flavoprotein subunit | MALDI | 18 | P31040 | |
| 109* | | | 23 | | |
| 110* | | | 14 | | |
| 111* | | | 38 | | |
| 112 | Heat shock protein 60 | MALDI | 35 | P19226 | Stress response |

Figure 6:
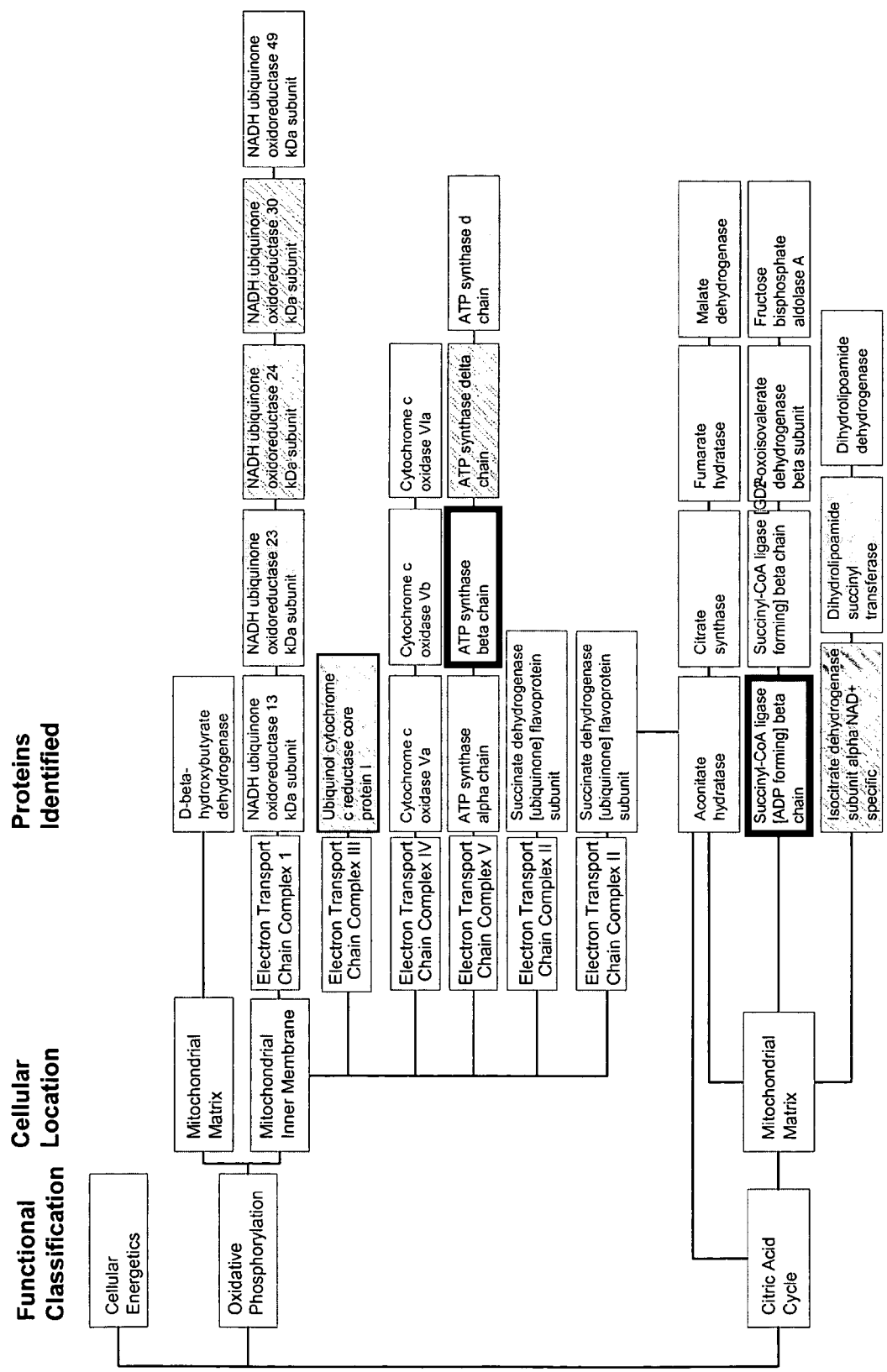
FIG. 6 shows a functional classification tree containing all proteins that have been identified by proteomic analysis. Proteins that are not modified by either drug (relative to controls) have white backgrounds. Proteins that do show significant change relative to controls are indicated as follows: proteins affected by adenosine are indicated by darker bordering; proteins affected by diazoxide are indicated by grey backgrounds; and proteins modified by both adenosine and diazoxide preconditioning are indicated by hatched grey backgrounds.
Figure 6:
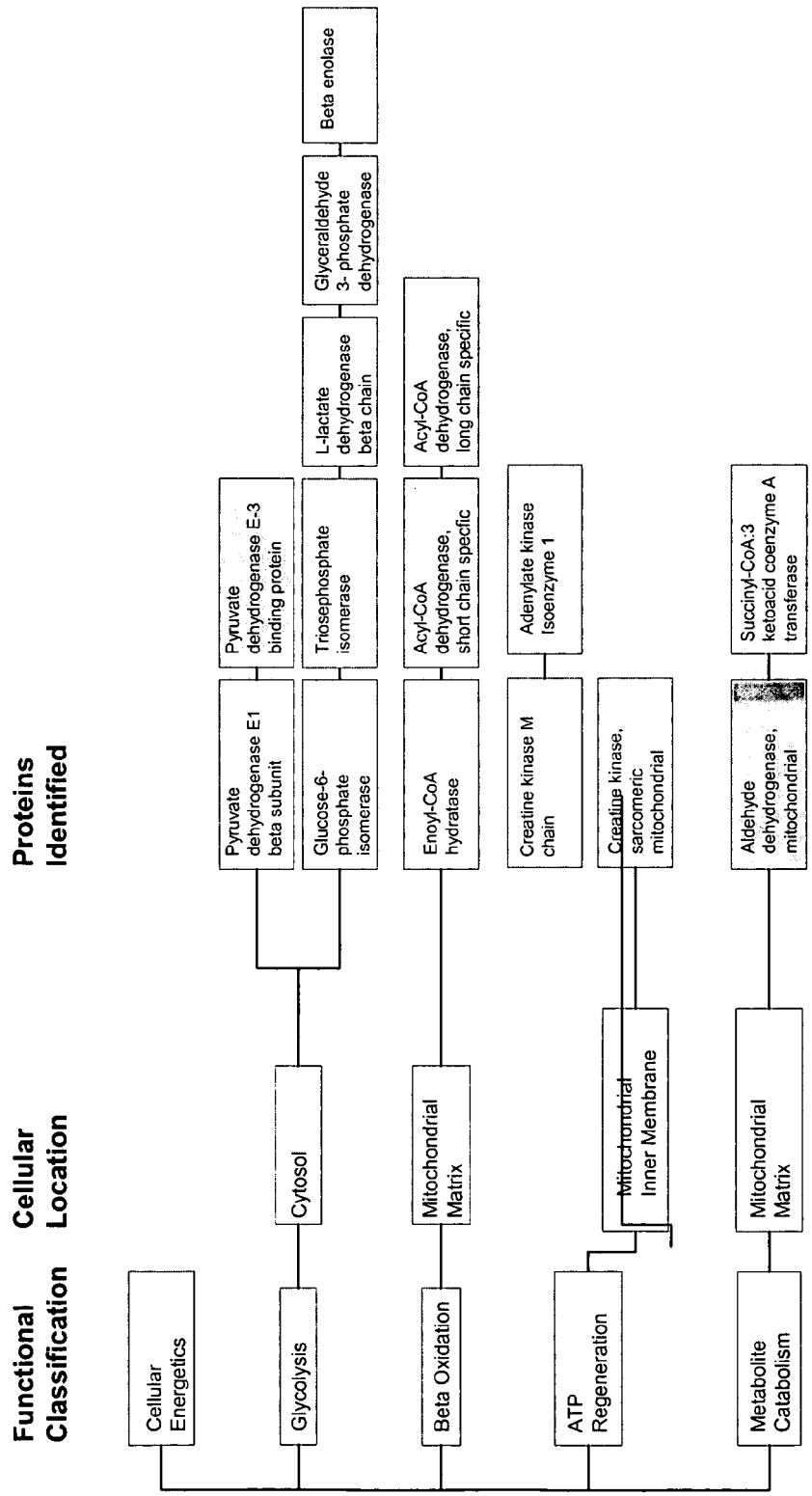
Figure 6:
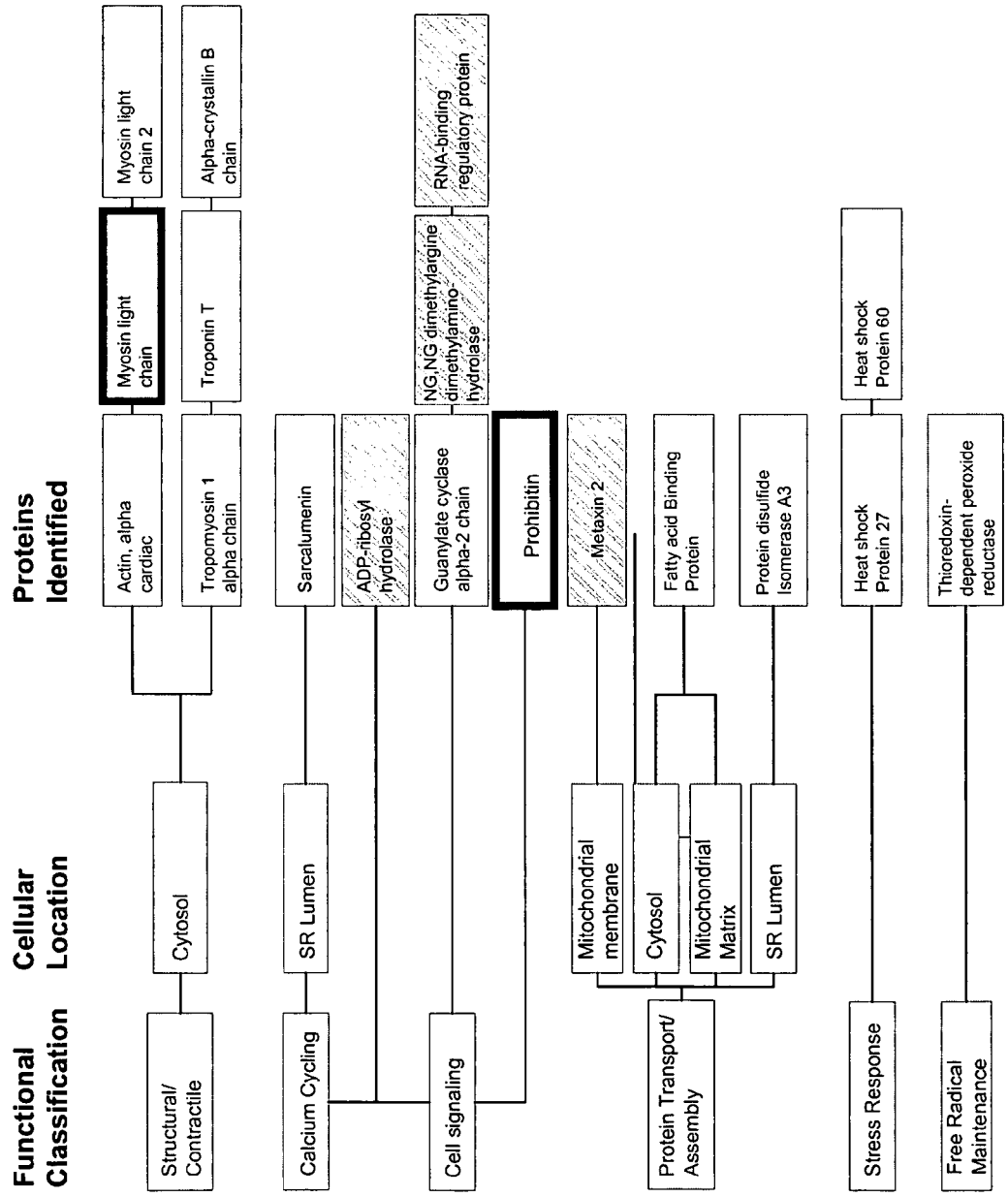

This revealed that while the adenosine- and diazoxide-induced protein changes identified here occurred to TCA cycle, OxPhos, chaperone proteins, $Ca^{2+}$ handling proteins, and to proteins selected from aldehyde dehydrogenase, NG-dimethylarginine dimethylaminohydrolase (DDAH) and the RNA binding protein regulatory subunit DJ-1, there were also additional proteins not detectably modified by preconditioning in these experiments (see FIG. 6) and thus not identified as preconditioning proteins as defined herein.

The identification of the preconditioning proteins described herein has provided a means for identifying and using compositions and methods for modulating these preconditioning proteins and priming cells for preconditioning and/or inducing and/or modulating preconditioning of a cell, tissue or organ.

Accordingly, an aspect of the present invention relates to compositions and methods or events for modulating a preconditioning protein such as the abundance of a TCA cycle enzyme and/or an OxPhos component and/or a chaperone protein and/or a $Ca^{2+}$ handling protein and/or a protein selected from aldehyde dehydrogenase, NG-dimethylarginine dimethylaminohydrolase (DDAH) and the RNA binding protein regulatory subunit DJ-1 in cells by administering to the cells compositions or subjecting the cells to a method or event which is known to induce preconditioning of organs such as the heart, skeletal muscle, smooth muscle, brain, kidney and/or liver. For example, as shown herein, preconditioning proteins are modulated by treating cells with a pharmacological preconditioning agent. It is expected that these preconditioning proteins can be modulated similarly by exposing the cells to an event such as brief ischemic or hypoxic episode. Modulations in preconditioning proteins expected with the compositions, methods and/or events of the present invention include, but are not limited to one or more of the following changes:

an increase in level of IDH; succinyl CoA ligase; the 23 kDa subunit, 24 kDa subunit, and/or 30 kDa subunit (mitochondrial precursors) of Complex I; the δ chain (mitochondrial precursor) of the $F_1$ portion, and/or the d chain (mitochondrial precursor) of the $F_0$ portion of Complex V; prohibitin; ADP ribosyl hydrolase; HSP27; and/or the RNA binding protein regulatory subunit (DJ-1);

a decrease in level of dihydrolipoamide succinyltransferase; core protein I of Complex III; metaxin 2; and/or sarcalumenin;

a change (increase or decrease) in the level of DDAH; and/or an increase in the post-translational modification of β chain (mitochondrial precursor) of the $F_1$ portion of Complex V; protein X; and/or aconitate hydratase (aconitase).

Another aspect of the present invention relates to methods for the identification of new compositions and methods or events useful in modulating a preconditioning protein and/or in priming a cell for preconditioning and/or inducing or modulating preconditioning of a cell, tissue organ. Such new compositions, methods or events can be identified routinely in accordance with the teachings herein based upon their ability to modulate one or more of the preconditioning proteins identified herein. Modulation of one or more of the preconditioning proteins can be assessed in a cell, tissue or organ by detection of one or more of the proteins in the presence and absence of the composition, method or event. A change in the abundance or partitioning of the protein itself and/or post-translational product of the protein in the cell, tissue or organ in the presence of the composition, upon exposure of the cell, tissue or organ to the method or event, as compared to a cell, tissue or organ in the absence of the composition or a cell, tissue or organ not exposed to the method or event is indicative of the composition, method or event modulating the preconditioning protein and/or priming the cell for preconditioning and/or inducing or modulating preconditioning of a cell, tissue or organ. Preferred compositions, methods or events of the present invention will produce one or more of the following changes:

an increase in level of IDH; succinyl CoA ligase; the 23 kDa subunit, 24 kDa subunit, and/or 30 kDa subunit (mitochondrial precursors) of Complex I; the δ chain (mitochondrial precursor) of the $F_1$ portion, and/or the d chain (mitochondrial precursor) of the $F_0$ portion of Complex V; prohibitin; ADP ribosyl hydrolase; HSP27; and/or the RNA binding protein regulatory subunit (DJ-1);

a decrease in level of dihydrolipoamide succinyltransferase; core protein I of Complex III; metaxin 2; and/or sarcalumenin;

a change (increase or decrease) in the level of DDAH; and/or an increase in the post-translational modification of β chain (mitochondrial precursor) of the $F_1$ portion of Complex V; protein X; and/or aconitate hydratase (aconitase).

More preferred are compositions, methods or events that mimic the modulation of the preconditioning proteins by adenosine or diazoxide. Most preferred are compositions comprising small organic molecules. Such small organic molecules can be designed to have similar structure and therefore similar activity to adenosine or diazoxide. Alternatively, screening assays for small organic molecules with similar function to adenosine or diazoxide in modulating preconditioning proteins in cells can be used to identify compositions of the present invention.

Compositions, methods and/or events identified as modulating a preconditioning protein are expected to be useful in priming a cell for preconditioning and/or as preconditioning agents. Accordingly, another aspect of the present invention relates to regulation of a preconditioning protein as a means for priming cells for preconditioning and/or preconditioning a cell, tissue or organ and preventing cell injury and/or cell death upon an ischemic and/or hypoxic episode. As each of the preconditioning proteins are involved in important cellular processes, compositions, methods and/or events can also be used to monitor and/or modulate one or more of the cellular processes, i.e. TCA cycling, oxidative phosphorylation, $Ca^{2+}$ handling, chaperones, and/or modulating a protein selected from aldehyde dehydrogenase, NG-dimethylarginine dimethylaminohydrolase (DDAH) and the RNA binding protein regulatory subunit DJ-1. Understanding the effects of modulation of the preconditioning proteins and/or the cellular processes in which they are involved will lead to better treatment of patients suffering from cell injury or cell death such as that caused by ischemia-reperfusion or hypoxic-reperfusion injury. For example, following cardiac arrest during surgery there are little or no free nucleotides left in myocytes and acidity (hydrogen ion content) of the cells is increased. In some cases, adenosine is added to stimulate ATP synthesis. This may only aid in the short term if adenosine also causes a reduction in the quantity of the functioning $F_1F_0$ ATPase in the mitochondria with time (time being required for the modified β-chain to be incorporated into the mature complex). Long term treatment thus may require blocking or eliminating adenosine action subsequent to obtaining its beneficial short term effects.

Alternatively, if modulation of TCA cycle enzymes and/or OxPhos proteins and/or chaperone proteins and/or $Ca^{2+}$ handling proteins and/or proteins selected from aldehyde dehydrogenase, NG-dimethylarginine dimethylaminohydrolase (DDAH) and the RNA binding protein regulatory subunit DJ-1 are demonstrated to be beneficial in that they enhance or reduce the activity of oxidative metabolism during a subsequent ischemia such that during reperfusion following ischemia the extent of cell death via necrosis and/or apoptosis is reduced, then further promotion of the modifications via administration of additional adenosine or diazoxide (or equivalent agents) may be desired.

Further, as shown herein, different pharmacological preconditioning agents caused different modifications of these preconditioning proteins. For example, pharmacological preconditioning with diazoxide resulted in an increase in IDH; the 23, 24, and 30 kDa subunits (mitochondrial precursors) of Complex I; the δ chain (mitochondrial precursor) of the $F_1$ portion, and the d chain (mitochondrial precursor) of the $F_0$ portion of Complex V; ADP ribosyl hydrolase; DDAH; HSP27; RNA binding protein regulatory subunit (DJ-1); and post-translational modification of protein X; and a decrease in core protein I of Complex III; dihydrolipoamide succinyltransferase; metaxin 2; and sarcalumenin. Pharmacological preconditioning with adenosine resulted in an increase in IDH; succinyl CoA ligase; the 24 and 30 kDa subunits (mitochondrial precursors) of Complex I; the δ chain (mitochondrial precursor) of the $F_1$ portion of Complex V; and the post-translational modification of the β chain (mitochondrial precursor) of the $F_1$ portion of Complex V; prohibitin; ADP ribosyl hydrolase; and RNA binding protein regulatory subunit (DJ-1); and a decrease in core protein I of Complex III; metaxin 2; and DDAH. Accordingly, preconditioning agents may be sub-categorized based upon their ability to modulate different preconditioning proteins identified herein. Such sub-categorization will be useful in selecting varying treatment regimes, particularly for patients on long-term therapy wherein desensitization to a single preconditioning agent is oftentimes observed. Accordingly, individuals at greater risk of an ischemic event can be maintained in a long-term preconditioned state without desensitizing them to preconditioning agents, by selectively administering different subcategories of preconditioning agents that, while having the same end effect of protecting cells, tissues or organs from death, do not necessarily act on the exact same proteins to confer this protection.

Another aspect of the present invention relates to methods for diagnosing and/or monitoring in a subject preconditioning and/or ischemic, hypoxic, ischemic/reperfusion or hypoxic/reperfusion conditions and/or the ability of a cell, tissue or organ to survive injury by monitoring modulation of one or more of the preconditioning proteins. One or more of the preconditioning proteins may be detected in a sample of injured cells, tissue or organ as well as in a biological fluid such as, for example, blood, serum, plasma, urine, bile, saliva, semen, mucus or cerebrospinal fluid, obtained from the subject.

In one embodiment of this aspect of the present invention, levels of a preconditioning protein can be monitored in a subject to assess whether a cell, tissue or organ has been subjected to sufficient preconditioning or requires additional preconditioning for protection from cell, tissue or organ injury or death.

Diagnosis of an ischemic or hypoxic condition can also be performed by comparing levels of a preconditioning protein measured in a subject with levels of this protein in a control. A difference in levels of a preconditioning protein in the subject as compared to the control is indicative of an ischemic or hypoxic condition in the subject. Differences in preconditioning proteins diagnostic of an ischemic or hypoxic condition include:

an increase in level of IDH; succinyl CoA ligase; the 23 kDa subunit, 24 kDa subunit, and/or 30 kDa subunit (mitochondrial precursors) of Complex I; the δ chain (mitochondrial precursor) of the $F_1$ portion, and/or the d chain (mitochondrial precursor) of the $F_0$ portion of Complex V; prohibitin; ADP ribosyl hydrolase; HSP27; and/or the RNA binding protein regulatory subunit (DJ-1);

a decrease in level of dihydrolipoamide succinyltransferase; core protein I of Complex III; metaxin 2; and/or sarcalumenin;

a change (increase or decrease) in the level of DDAH; and/or an increase in the post-translational modification of β chain (mitochondrial precursor) of the $F_1$ portion of Complex V; protein X; and/or aconitate hydratase (aconitase).

As used herein, by "control" it is meant, a sample obtained from an individual known not have an ischemic or hypoxic condition, a sample obtained previously from the subject prior to the onset or suspicion of the ischemic or hypoxic condition, or a standard from data obtained from a data bank corresponding to currently accepted normal levels of the preconditioning protein. One or more of: an increase in level of IDH; succinyl CoA ligase; the 23 kDa subunit, 24 kDa subunit, and/or 30 kDa subunit (mitochondrial precursors) of Complex I; the δ chain (mitochondrial precursor) of the $F_1$ portion, and/or the d chain (mitochondrial precursor) of the $F_0$ portion of Complex V; prohibitin; ADP ribosyl hydrolase; HSP27; and/or the RNA binding protein regulatory subunit (DJ-1); a decrease in level of dihydrolipoamide succinyltransferase; core protein I of Complex III; metaxin 2; and/or sarcalumenin; a change (increase or decrease) in the level of DDAH; and/or an increase in the post-translational modification of β chain (mitochondrial precursor) of the $F_1$ portion of Complex V; protein X; and/or aconitate hydratase (aconitase) are indicative of the subject having an ischemic or hypoxic condition. The comparison performed may be a straight-forward comparison, such as a ratio, or it may involve weighting of one or more of the measures relative to, for example, their importance to the particular situation under consideration. The comparison may also involve subjecting the measurement data to any appropriate statistical analysis.

The following nonlimiting examples are provided to further illustrate the present invention.

EXAMPLES

Example 1

Isolation and Preconditioning of Rabbit Ventricular Myocytes

Ventricular myocytes from New Zealand White rabbits (weighing 1 to 2 kg) were isolated by collagenase dissociation, as described previously by Liu et al. (Circ. Res. 1996 78:443–454). Hearts were excised, then perfused with collagenase (1.0 mg/mL, Worthington type II) for 14 minutes at a maintained perfusion pressure of 75 mm Hg on a Langendorff apparatus, yielding>50% $Ca^{2+}$-tolerant ventricular myocytes. Cell isolation was followed directly by pharmacological preconditioning, which was carried out by treatment with 100 μmol/L adenosine (Sigma) or with 100 μmol/L diazoxide (Sigma) for 60 minutes in a 37° C. water bath, as described previously by Liu et al. supra. Untreated cells were prepared concurrently as drug-free controls. Equivalent 25 μL aliquots of cells (containing ~30 mg/mL of protein as determined by Lowry assay (Lowry, O. H. J. Biol. Chem. 1951 193:265–275) were frozen and stored at −80° C. until analysis.

Example 2

In Sequence Protein Extraction and Subcellular Fractionation

Figure 3:
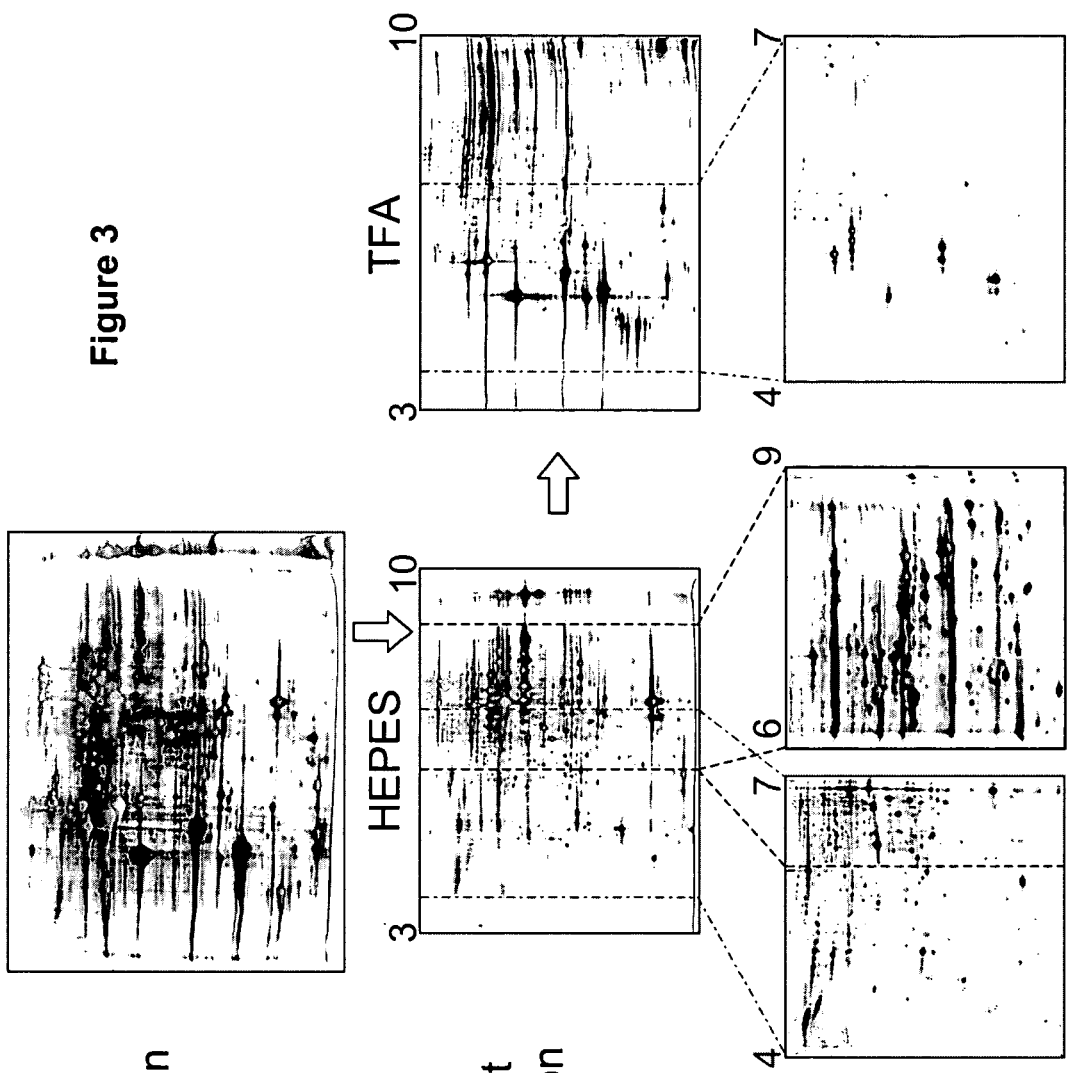
FIG. 3 shows a schematic of the multi-tiered two-dimensional gel electrophoresis approach used for protein separation and analysis. The whole tissue gel (top) shows the complexity of attempting to homogenize and resolve all proteins simultaneously. To simplify the ventricular myocyte protein profile and to facilitate subsequent detection and analysis of protein changes induced by adenosine and diazoxide preconditioning, a pH-dependent sequential subfractionation was carried out to first obtain two separate subproteomes, the HEPES extract at pH 7.4, followed by the TFA extract at pH 2.0 (middle panels). Analysis was further enhanced by then focusing on specific proteins of interest by the application of different pH gradient zoom gels (bottom), to focus on proteins in a specific pH range, and by using multiple protein loads, to analyze either high abundance proteins (at low loads) or to look for changes to low abundance proteins (at high protein loads).
Figure 4A:
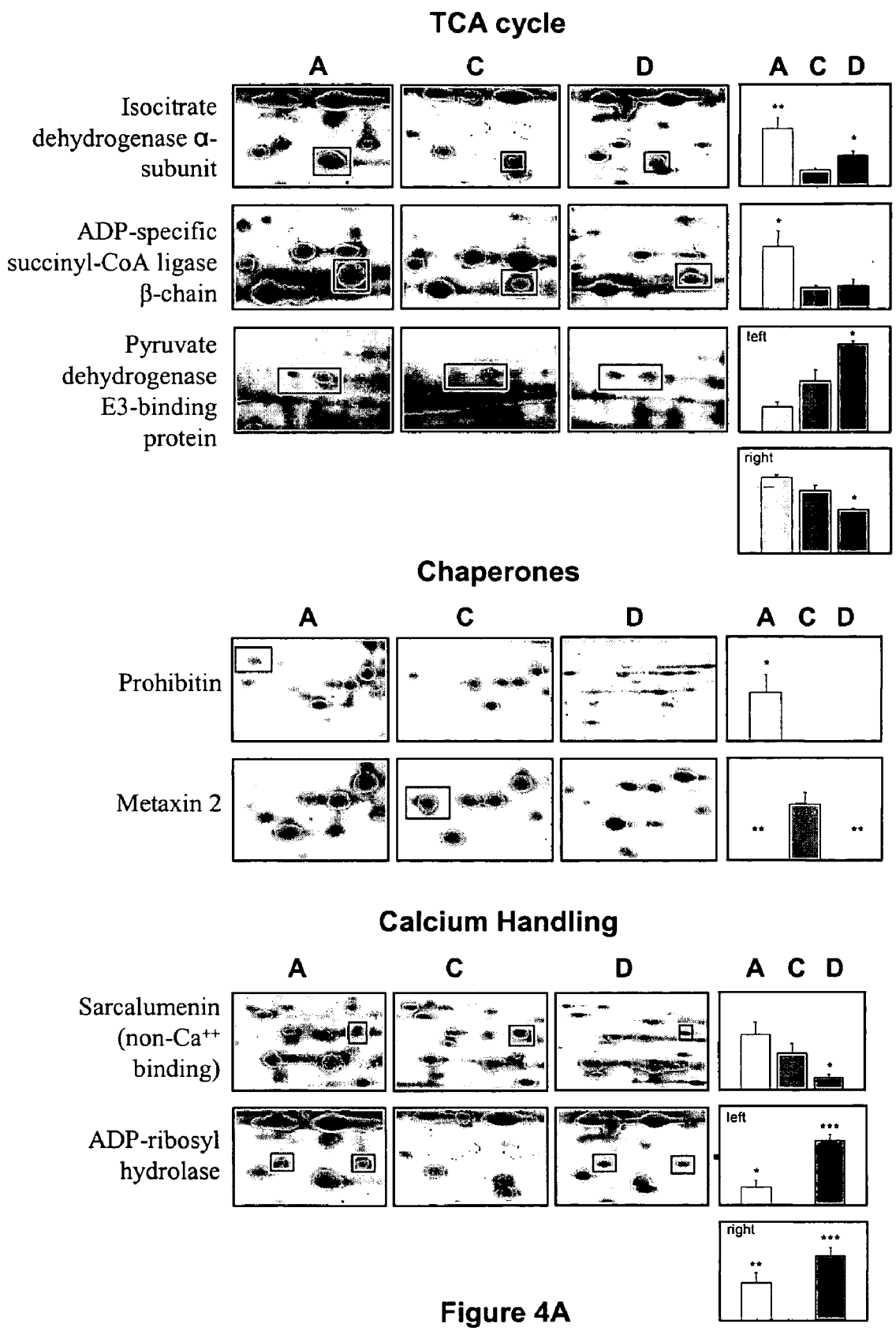
FIGS. 4A through 4C show identical regions of silver-stained two-dimensional gels to indicate the intra-gel positions of protein spots that have been identified as changing between pharmacologically preconditioned and untreated rabbit ventricular myocytes from 2-D gels of equivalent protein loads from extracts of each treatment (A=adenosine; C=control; D=diazoxide). For each protein, its location within the adjacent gel image, if present, is indicated by a box. Modified proteins are grouped by cellular function into the following categories: TCA cycle, chaperones, calcium handling (FIG. 4A); oxidative phosphorylation (FIG. 4B); late preconditioning, and two examples of unmodified proteins included for comparison (FIG. 4C). The graphs to the right of the gel images indicate the relative abundance of the protein for each treatment (again, A=adenosine; C=control; D=diazoxide), and spots which show statistically significant change relative to the corresponding control, are indicated (*$P<0.05$, $P<0.01$, or *$P<0.001$, using a two-tailed student's t test to analyze one gel per rabbit, with n=4 rabbits per treatment).
Figure 4B:
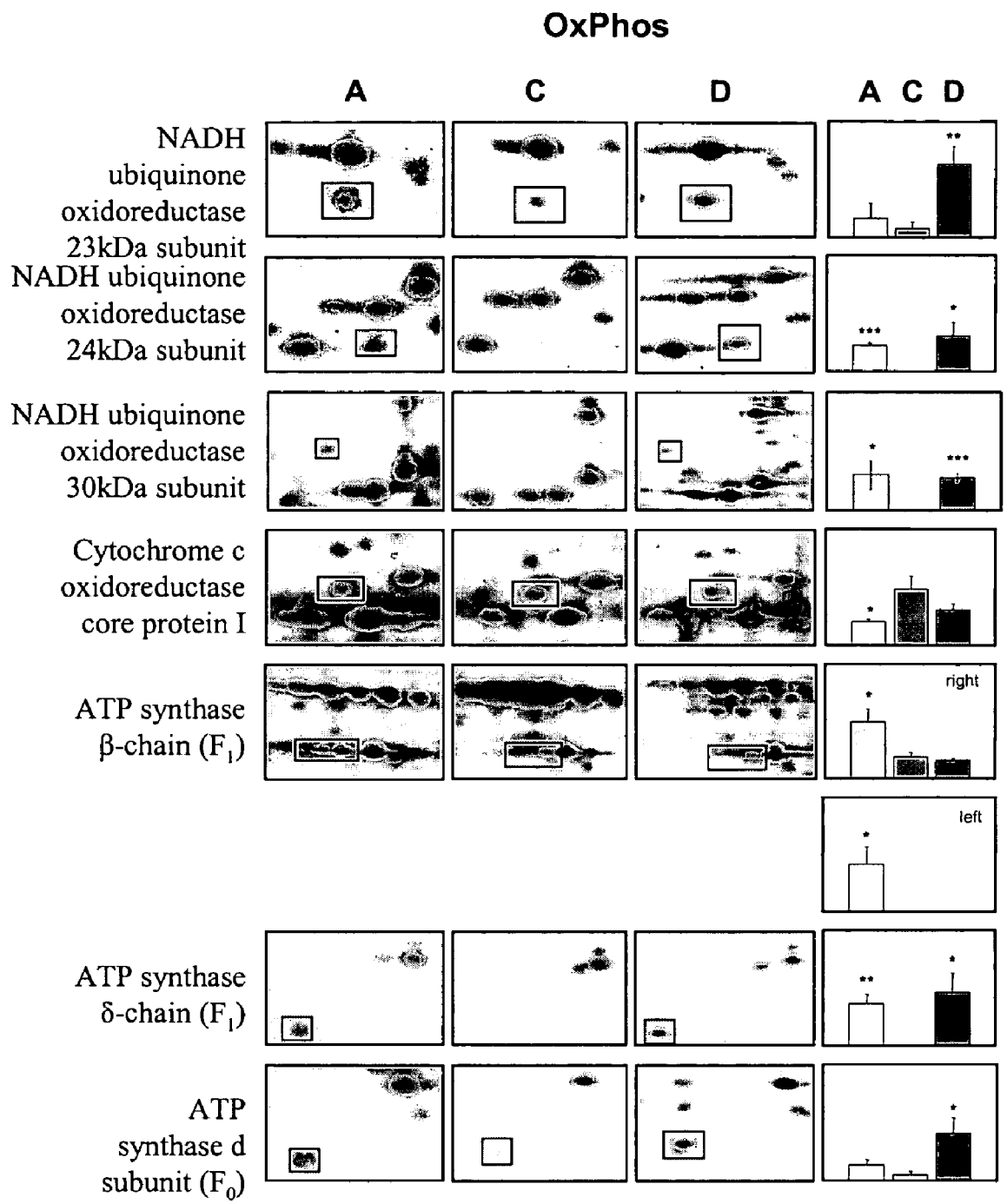
Figure 4C:
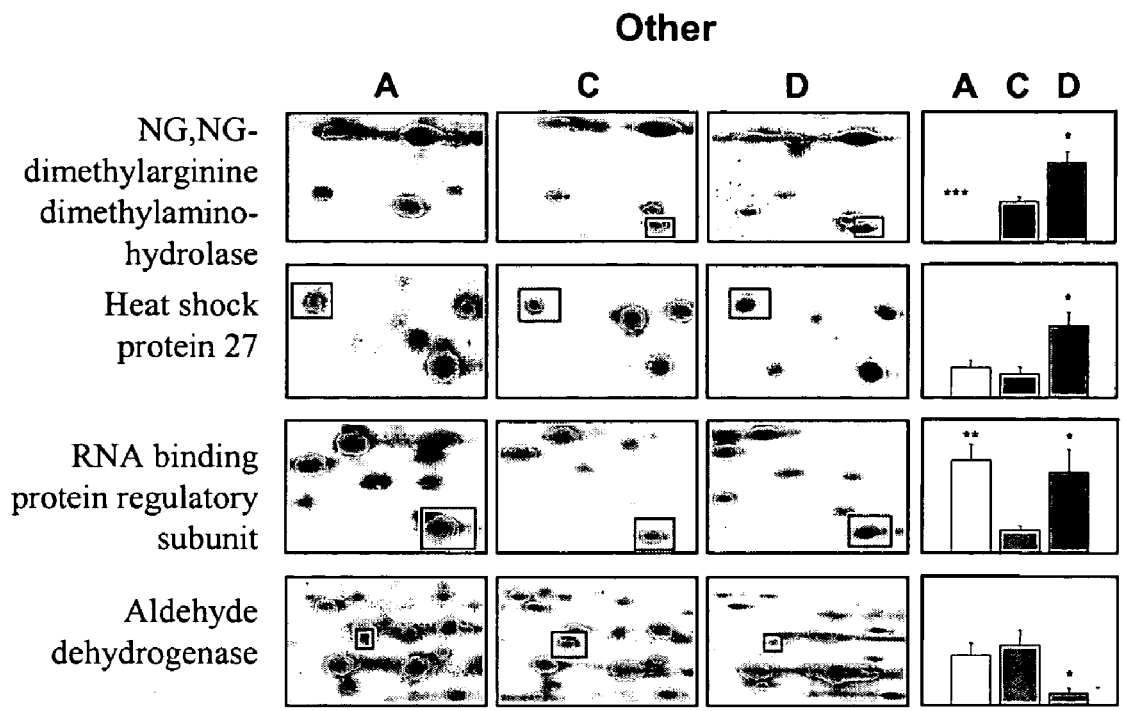
Figure 4C:
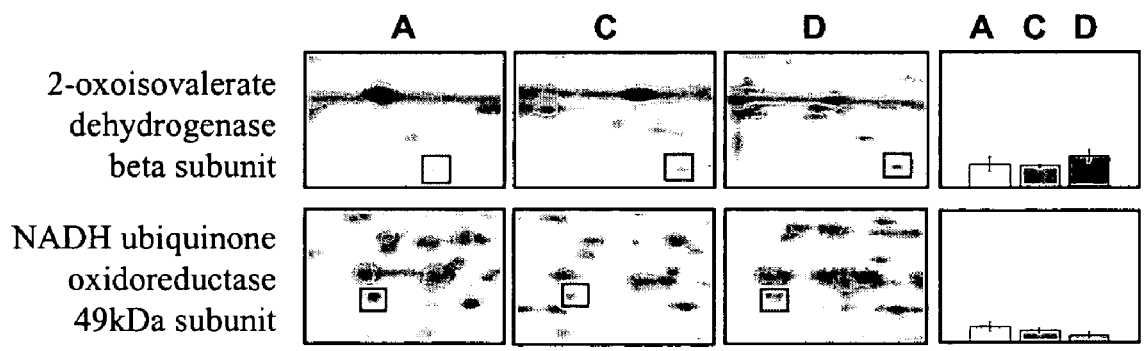

All steps in this Protein extraction protocol, referred to herein as "In Sequence" and depicted in FIG. 3, produce physiological pH (cytosolic) and acidic pH enriched extracts were carried out at 4° C., and all centrifugations were conducted at 16000×g for 2 minutes at 4° C. Myocyte proteins were first extracted by two rounds of homogenization in 100 μL of HEPES extraction buffer, consisting of (in mmol/L) HEPES 25 (pH 7.4), NaF 50, $Na_3VO_4$ 0.25, phenylmethylsulfonyl fluoride 0.25, EDTA 0.5, and (in μmol/L) leupeptin 1.25, pepstatin A 1.25. Following homogenization and centrifugation, the supernatants were pooled and saved as the cytosolic extract. The remaining pellet was subjected to further extraction by two rounds of homogenization in 50 μL of acid extraction buffer, consisting of 1% v/v trifluoroacetic acid (TFA) and 1 mmol/L Tris(2-carboxyethylphosphine)hydrochloride (pH ~2.0). Supernatants were again pooled, and saved as the acid extract. The two extracts and remaining pellet were frozen and stored at −80° C.

Example 3

Two-Dimensional Gel Electrophoresis (2-DE)

Isoelectric focusing (IEF) of cytosolic and TFA extracts were carried out using a Protean® IEF cell (Bio-Rad) according to the manufacturer's protocol. Protein loads ranging from 5 up to 250 μg per gel were added to the following rehydration buffers: for cytosolic extracts, 8 M urea, 2.5 M thiourea, 4% CHAPS, 2 mM EDTA, and 25 mM DTT, and in the case of pH 6–9 strips, CHAPS and DTT were substituted by 4% ASB-14 and 5.4% (w/v) 2-hydroxyethyl disulfide, respectively; for acidic extracts, 8 M urea, 4% CHAPS, and 25 mM DTT. Immobilized pH gradient (IPG) Ready Strips™ (170 mm pH 4–7, 6–9, or 3–10 linear gradient, Bio-Rad) were actively rehydrated at 50 volts (V) for 10 hours to enhance protein uptake, then subjected to the following conditions using a rapid voltage ramping method: 100 V for 25 Volt-hours (Vh), 500 V for 125 Vh, 1000 V for 250 Vh, and 8000 V for 65 kVh. A Peltier temperature control platform maintained gels at 20° C. throughout IEF. Focused gels were stored at −20° C. prior to sodium dodecyl sulfate-polyacrylamide gel electrophoresis (SDS-PAGE).

For SDS-PAGE, IPG strips were incubated for 10 minutes in equilibration buffer (50 mmol/L Tris-HCl, pH 8.8, 6 mol/L urea, 30% v/v glycerol, 2% w/v SDS) supplemented with 10 mg/mL DTT, followed by a 10 minute incubation in equilibration buffer supplemented with 25 mg/mL iodoacetamide, then rinsed once with SDS-PAGE buffer (25 mmol/L Tris, 192 mmol/L glycine, pH 8.3, 0.1% w/v SDS). IEF strips were then embedded in a 5% acrylamide stacking gel and the proteins were resolved by 10 or 12.5% SDS-PAGE using a Protean® II XL system (Bio-Rad). Electrophoresis was carried out until the dye front reached the bottom of the resolving gel (50 V for 30 minutes until proteins were transferred from the IPG strips to the stacking gel, followed either by 150 V for 7.5 hours or by 250 V for 4 hours).

Example 4

Protein Transfer and Western Blotting

Following 2-DE, gels were equilibrated in SDS-PAGE buffer supplemented to 20% v/v methanol for 10 minutes, then transferred in the same buffer to nitrocellulose at 200 mA constant current for 2 hours. Nitrocellulose membranes were then rinsed with phosphate-buffered saline/Tween-20 (PBS/T), consisting of (in mmol/L) NaCl 137, KCl 2.7, $Na_2HPO_4$ 10.1, $KH_2PO_4$ 1.8, pH 7.4 supplemented to 0.1% v/v Tween-20, then blocked overnight at 4° C. with 1% v/v blocking reagent (Roche Diagnostics) in PBS/T. Western blotting for ATP synthase β-chain was performed at 1 μg/mL with the anti-ATP synthase β-chain antibody Clone No. 7E3-F2 (Molecular Probes Cat. No. A-21299, Eugene, Oreg.), and detected by chemiluminescence with an alkaline phosphatase-conjugated secondary antibody.

Example 5

Silver Staining of Two-Dimensional Gels

Two-dimensional gels were silver stained according to the protocol of Shevchenko et al. (Anal. Chem. 1996 68:850–858) for compatibility with subsequent analysis of proteins by mass spectrometry. Gels were fixed overnight in 50% v/v methanol, 5% v/v acetic acid, followed by 50% v/v methanol for 10 minutes, then 10 minutes in deionized distilled (dd) $H_2O$. Gels were sensitized for 1 minute in 0.02% w/v sodium thiosulfate, followed by two 1-minute dd$H_2O$ washes, then incubated in chilled (4° C.) 0.1% w/v silver nitrate for 20 minutes, followed again by two 1-minute dd$H_2O$ washes. Proteins were then visualized by several washes with developing solution (2% w/v sodium carbonate, 0.04% v/v formalin) until maximum staining was obtained without a concomitant increase in background staining, after which development was stopped with 5% v/v acetic acid.

Example 6

Image Analysis and Quantification

Silver-stained 2-D gels were digitized at 150 dpi (pixels per inch) resolution using a PowerLookII® scanner (UMAX® Data Systems, Inc.) on a Sun® Ultra5™ computer (Sun Microsystems, Inc.). Protein spots were then located, quantified, and matched to spots on other gels using Investigator™ HT Proteome Analyzer 1.0.1 software (Genomic Solutions, Inc.). A number of manually defined spots were selected as anchors (preferably 15 or more) for triangulation of remaining spots. Composite images were then prepared by matching spots from four gel images for each treatment group (adenosine, diazoxide, and control). Protein spot normalization (for n=4) was carried out by using total spot intensity ratio to normalize gel staining across treatments and animals, or by using a match ratio method for determination of the extent of modification for protein spots from post-translationally modified proteins.

Example 7

Mass Spectrometry Protein Preparation

Protein spots extracted from 2-D gels were destained according to Gharahdaghi et al. (Electrophoresis 1999 20:601–605), then dried under vacuum before enzymatic digestion with sequence-grade modified trypsin (Promega) or Asp-N (Sigma). Peptides were extracted with 50% acetonitrile (ACN)/5% TFA, dried under vacuum, and reconstituted with 3 μL of 50% ACN/0.1% TFA. Reconstituted extract (0.5 μL) was mixed with 0.5 μL of matrix (10 mg/mL α-cyano-4-hydroxy-trans-cinnamic acid in 50% ACN, 0.1% TFA), spotted on a stainless steel 100-well mass spectrometry plate, and air-dried.

MALDI-TOF MS of Cytosolic and Mitochondrial Proteins:

Samples were analyzed using a Voyager® DE-Pro matrix-assisted laser desorption/ionization time-of-flight (MALDI-TOF) mass spectrometer (PerSeptive Biosystems) reflector equipped with a 337 nm nitrogen laser operated in the delayed extraction/reflector mode with an accelerating voltage of 20 kV, grid voltage setting of 72%, and a 50 ns delay. Five spectra (50–100 laser shots/spectrum) were obtained for each sample. External calibration was performed using a Sequazyme Peptide Mass Standard kit (PerSeptive Biosystems) containing the following standards: des-Arg-bradykinin, angiotensin-1, and Glu-fibrinopeptide B.

MALDI-QTOF MS/MS:

MALDI MS/MS spectra were collected on an Applied Biosystems/MDS-Sciex QSTAR pulsar QTOF instrument (Concord, Ontario, Canada) equipped with an orthogonal MALDI source employing a 337 nm nitrogen laser. The instrument was operated in positive mode and collision-induced dissociation (CID) of peptides was achieved with argon as the collision gas. Spectra were acquired and processed using Sciex support software.

Example 8

Bioinformatic Data Analysis

Peptide mass fingerprinting was conducted with the database search tool MS-Fit in the program Protein Prospector, to search the Swiss-Prot protein database. A number of restrictions were applied to the search: species=mammals, pI range variable (depending on spot of interest), mass range variable (usually with 50–100 ppm mass tolerance), with a minimum of 4 peptides to match, and a maximum of one missed tryptic or Asp-N cleavage, with possible modifications including Cys-carbamidomethylation, Met-oxidation, protein N-terminal acetylation, and acrylamide modified Cys.

What is claimed is:

1. A method for identifying an agent which primes a cell for preconditioning and/or inducing preconditioning of a cell, tissue, or organ comprising:
   a) obtaining a cell, tissue, or organ that comprises an endogenous preconditioning protein, selected from the group consisting of isocitrate dehydrogenase NAD+ specific subunit alpha, succinyl CoA ligase, 23 kDa mitochondrial precursor subunit of Complex I, 24 kDa mitochondrial precursor subunit of Complex I, 30 kDa mitochondrial precursor subunit of Complex I, δ chain of the $F_1$ portion of Complex V, d chain of the $F_0$ portion of Complex V, prohibitin, ADP ribosyl hydrolase, HSP27 and RNA binding protein regulatory subunit (DJ-1);
   b) providing the agent to said cell, tissue, or organ;
   c) detecting an increase in abundance of the preconditioning protein in the presence of the agent as compared to the abundance of preconditioning protein in the absence of the agent; and thereby
   d) identifying an agent that primes a cell for preconditioning and/or inducing preconditioning of a cell, tissue, or organ.

2. A method for identifying an agent which primes a cell for preconditioning and/or inducing preconditioning of a cell, tissue, or organ comprising:
   a) obtaining a cell, tissue, or organ that comprises an endogenous preconditioning protein, selected from the group consisting of dihydrolipoamide succinyltransferase, core protein I of Complex III, metaxin 2 and sarcalumein;
   b) providing the agent to said cell, tissue, or organ;
   c) detecting a decrease in abundance of the preconditioning protein in the presence of the agent as compared to the abundance of preconditioning protein in the absence of the agent; and thereby
   d) identifying an agent that primes a cell for preconditioning and/or inducing preconditioning of a cell, tissue, or organ.

3. A method for identifying an agent which primes a cell for preconditioning and/or inducing preconditioning of a cell, tissue, or organ comprising:
  a) obtaining a cell, tissue, or organ that comprises an endogenous preconditioning protein, selected from the group consisting of the β chain of the $F_1$ portion of Complex V or protein X;
  b) providing the agent to said cell, tissue, or organ;
  c) detecting an increase in post-translational modification of the preconditioning protein in the presence of the agent as compared to the post-translational modification of the preconditioning protein in the absence of the agent; and thereby
  d) identifying an agent that primes a cell for preconditioning and/or inducing preconditioning of a cell, tissue, or organ.

4. The method of claim 1 wherein the preconditioning protein is isocitrate dehydrogenase NAD+ specific subunit alpha.

5. The method of claim 1 wherein the preconditioning protein is succinyl CoA ligase.

6. The method of claim 1 wherein the preconditioning protein is the 23 kDa mitochondrial precursor subunit of Complex I.

7. The method of claim 1 wherein the preconditioning protein is the 24 kDa mitochondrial precursor subunit of Complex I.

8. The method of claim 1 wherein the preconditioning protein is the 30 kDa mitochondrial precursor subunit of Complex I.

9. The method of claim 1 wherein the preconditioning protein is the δ chain mitochondrial precursor of the $F_1$ portion of Complex V.

10. The method of claim 1 wherein the preconditioning protein is the d chain of the $F_0$ portion of Complex V.

11. The method of claim 1 wherein the preconditioning protein is prohibitin.

12. The method of claim 1 wherein the preconditioning protein is ADP ribosyl hydrolase.

13. The method of claim 1 wherein the preconditioning protein is HSP27.

14. The method of claim 1 wherein the preconditioning protein is RNA binding protein regulatory subunit (DJ-1).

15. The method of claim 2 wherein the preconditioning protein is dihydrolipoamide succinyltransferase.

16. The method of claim 2 wherein the preconditioning protein is core protein I of Complex III.

17. The method of claim 2 wherein the preconditioning protein is metaxin 2.

18. The method of claim 2 wherein the preconditioning protein is sarcalumenin.

19. The method of claim 3 wherein the agent increases post-translational modification of the β chain of the $F_1$ portion of Complex V.

20. The method of claim 3 wherein the agent increases post-translational modification of protein x.

* * * * *

UNITED STATES PATENT AND TRADEMARK OFFICE
CERTIFICATE OF CORRECTION

PATENT NO.       : 7,195,890 B2  
APPLICATION NO. : 10/824027  
DATED            : March 27, 2007  
INVENTOR(S)      : Jennifer E. Van Eyk, Steven T. Elliott and David Kent Arrell Page 1 of 1

It is certified that error appears in the above-identified patent and that said Letters Patent is hereby corrected as shown below:

Column 24, Claim 2, Line 59
"sarcalumein" should be --sarcalumenin--;

Column 26, Claim 9, Line 2
"mitochondrial precursor" should be omitted.

Signed and Sealed this

Twenty-third Day of December, 2008

JON W. DUDAS
*Director of the United States Patent and Trademark Office*